United States Patent [19]

Terao et al.

[11] Patent Number: 5,665,770

[45] Date of Patent: Sep. 9, 1997

[54] METHOD FOR TREATMENT OF CATARACT WITH RADICAL SCAVENGER

[75] Inventors: Motome Terao, Hyogo-ken; Yoshimasa Ito, Nara-ken, both of Japan

[73] Assignee: Gakko Hojin Kinki Daigaku, Osaka, Japan

[21] Appl. No.: 335,351

[22] Filed: Nov. 3, 1994

[30] Foreign Application Priority Data

Nov. 5, 1993 [JP] Japan ................................. 5-277061

[51] Int. Cl.$^6$ ........................ A61K 31/27; A61K 31/41
[52] U.S. Cl. ........................ 514/476; 424/450; 424/489; 424/490; 424/491; 514/381
[58] Field of Search ........................ 514/476, 381; 424/450, 489, 490, 491

[56] References Cited

U.S. PATENT DOCUMENTS

| | | | |
|---|---|---|---|
| 4,347,371 | 8/1982 | Iwao et al. | 548/201 |
| 4,870,101 | 9/1989 | Ku et al. | 514/476 |
| 5,035,878 | 7/1991 | Borch et al. | 424/10 |
| 5,124,154 | 6/1992 | Babcock et al. | 424/427 |
| 5,174,988 | 12/1992 | Mautone et al. | 424/45 |
| 5,185,152 | 2/1993 | Peyman | 424/427 |
| 5,332,582 | 7/1994 | Babcock et al. | 424/78.04 |
| 5,338,545 | 8/1994 | Clark et al. | 424/94.1 |

OTHER PUBLICATIONS

Ito, Y., et al, Preparation of Liposomes Containing Disulfiram and Application of it as an Anti–cataract Agent, Abstract of Int. CCRG Congress, Bethesda, MD, Nov. 7–10, 1993, p. 55.

Arai, K., et al, J. Biol. Chem., 262, 16969–16972 (1987).

Arai, K., et al, Biochim. Biophys. Acta, 924, 292–296 (1987).

Epstein, D. L, et al, Invest. Ophthamol. 9, 629–638 (1970).

Merriam, G.R., et al., Radiat. Res., 62, 488–497 (1975).

Gupta, V.D., Am. J. Hosp. Pharm., 38, 363–364 (1981).

Agarwal, R. A., et al, Res. Comm. Chem. Pathol. Pharmacol. 42, 293–310 (1983).

Sakurai, T., et al, FEBS Letters, 236, 406–410 (1988).

Morimoto, K., et al, Arch. Int. Pharmacodyn., 293, 7–13 (1988).

Varma, S. D., et al, Ophthamic. Res. 14, 167–175 (1982).

Reddy, V. N., et al, Lens and Eye Toxic. Res., 6, 573–588 (1989).

Kuhnlein, U., Biochem. Biophys. Acta, 609, 75–82 (1980).

*Primary Examiner*—Gary Geist
*Assistant Examiner*—Barbara S. Frazier

[57] ABSTRACT

The invention provides a method for treatment of cataract which comprises administering to a subject in need of such treatment, a radical scavenger in an amount effective in treatment of cataract selected from the group consisting of a reducing thiol derivative, or a disulfide derivative and a sulfide derivative thereof, and a pharmaceutical composition for treatment of cataract which comprises an anti-cataract agent containing a radical scavenger and fine particles, such as emulsions, nanocapsules, alubmin microspheres and liposomes, which carries an anti-cataract agent and has a lipophilic and positively charged phase on the surface thereof.

23 Claims, 18 Drawing Sheets
(4 of 18 Drawing(s) in Color)

FIG. 10A
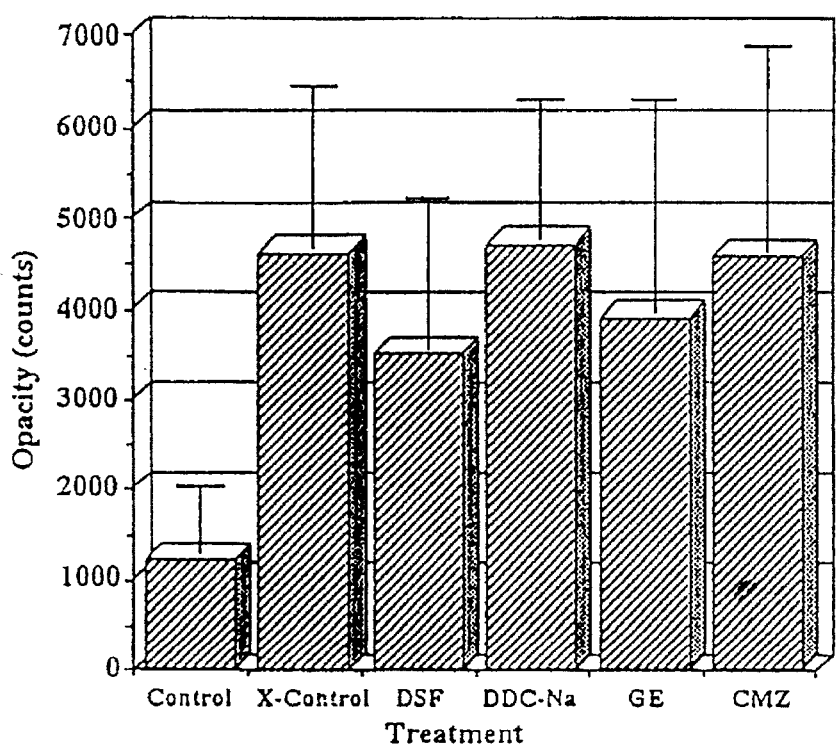
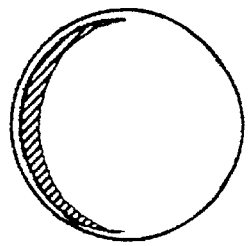
FIG. 10B
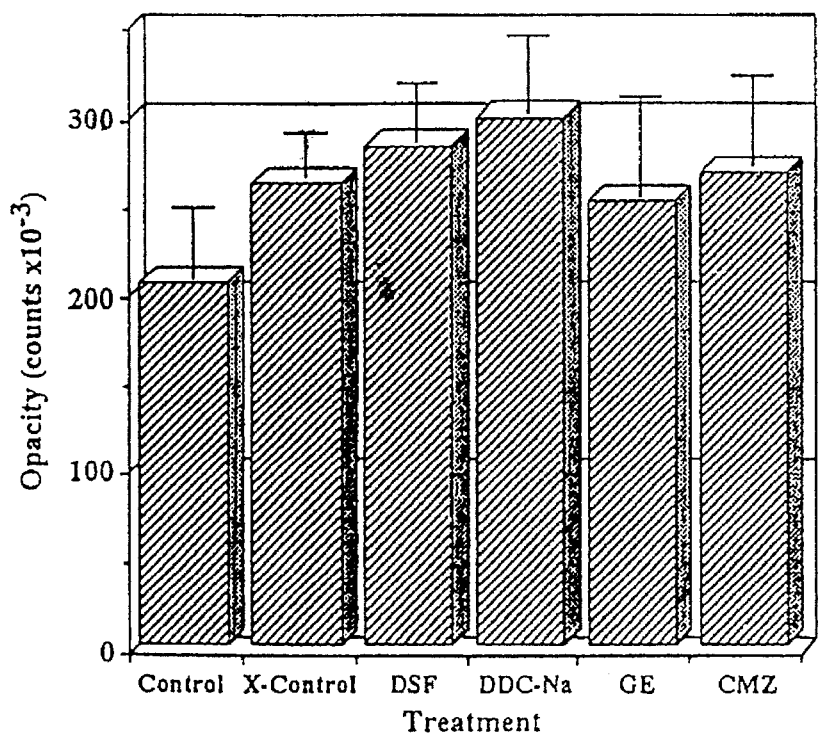
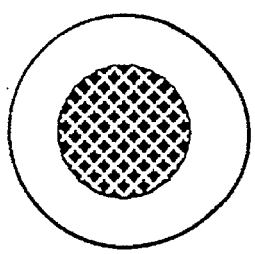

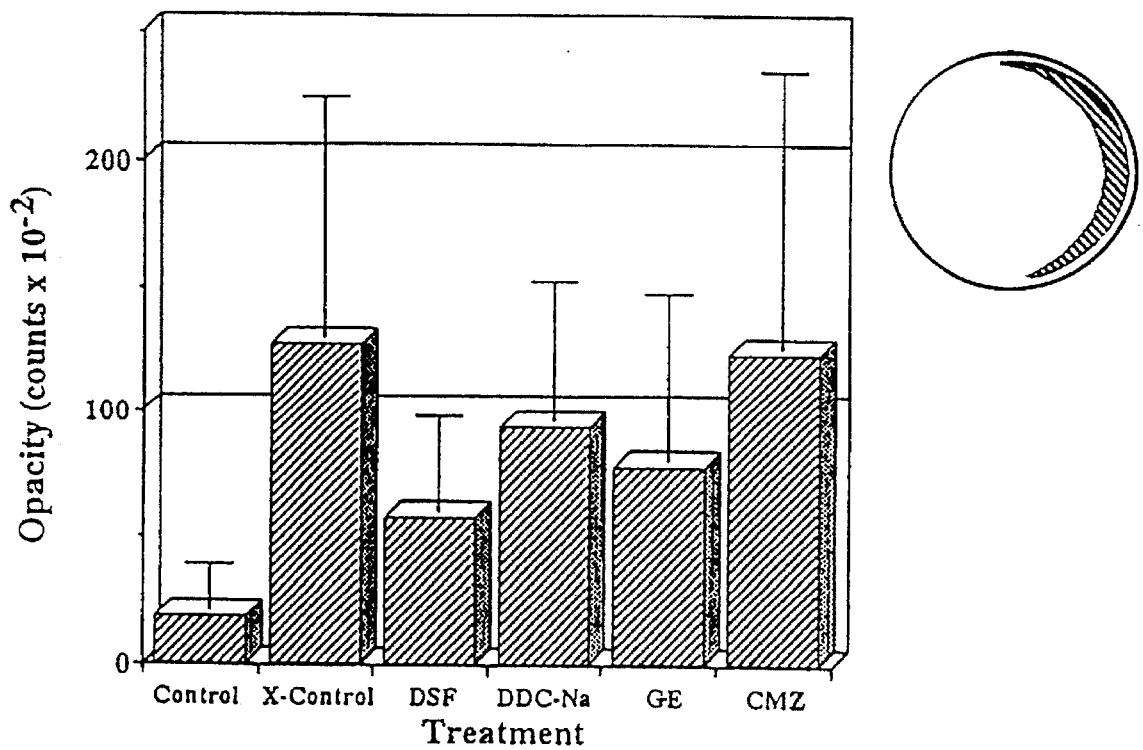
FIG. II

FIG. 17A
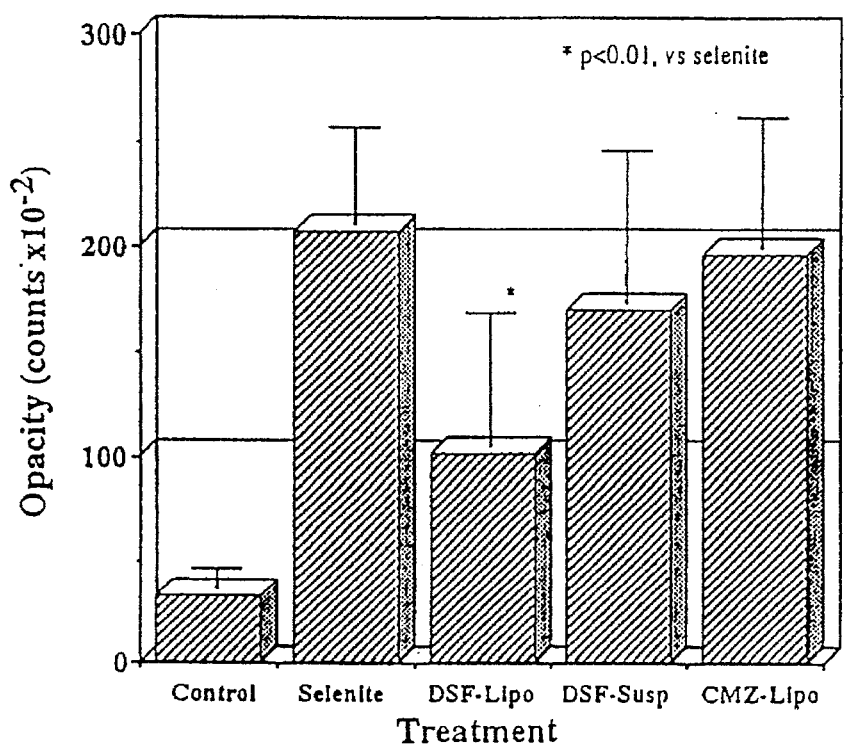
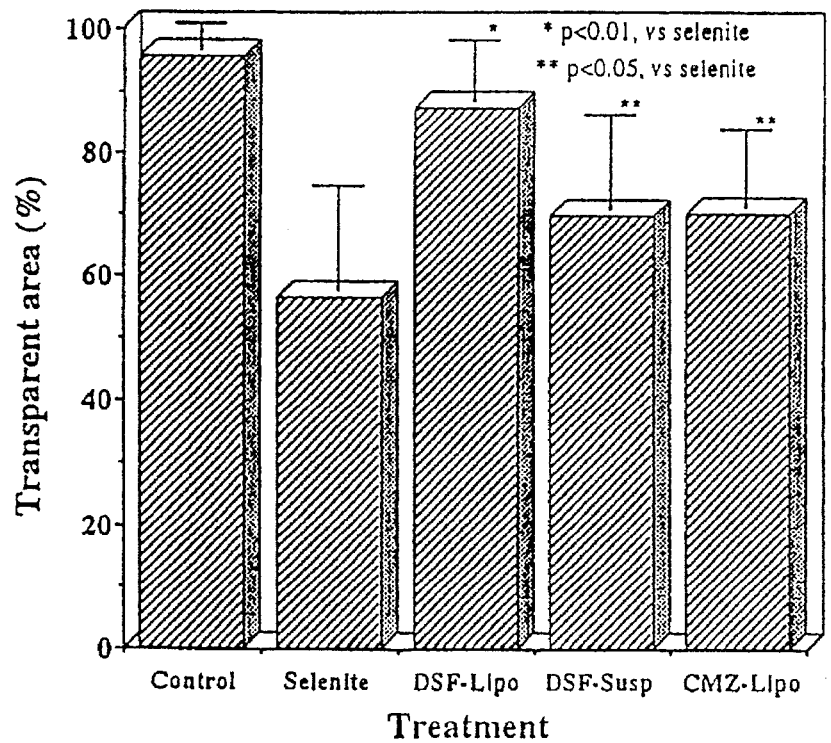
FIG. 17B

METHOD FOR TREATMENT OF CATARACT WITH RADICAL SCAVENGER

BACKGROUND OF THE INVENTION

1. Field of the Invention

The present invention relates to a method for treatment of cataract which comprises administering a radical scavenger such as a reducing thiol derivative, or a disulfide derivative or a sulfide derivative thereof.

2. Description of the Prior Art

In recent years, the incidense rate of senile cataract has been increasing with the increase in the rate of aged people in the population in Japan. Mechanisms of outbreak or progress of cataract have not been elucidated; however, it is now thought that pathogenic matter causes faculty in biological anti-oxidation system to generally grow weak and then lens proteins aggultinate to generate opacity in the lens. The faculty in biological anti-oxidation system seems to grow weak by the following mechanisms: (1) in the course of progress of cataract, generation of reaction system in which anti-oxidant in the lens is abnormally consumed; and (2) defluxion of glutatione (GSH) of reducing biocomponents by diffusion with other components in the lens due to abnormal transpenetration of membrane of the lens. Opacity of the lens is also suggested to be caused by change of ion balance of Na/K and irreversibility of ion balance by $Ca^{2+}$.

Aldose reductase inhibitors (ARIs) have been developed as anti-cataract agents for diabetic cataract and some effective compounds have been proposed in animal experiments. However, one of potential ARIs killed 3 patients in its clinical trial in the United States, therefore, this kind of anti-cataract agent was stopped from being used. A possible anti-cataract agent has been expected to be developed for a long time.

The inventors have studied as anti-cataract agents some inhibitors of the lowering of faculty in biological anti-oxidation system and the present invention was made in the course of that study.

SUMMARY OF THE INVENTION

The first object of the invention is to provide a radical scavenger selected from reducing thiol derivatives or disulfide derivatives and sulfide derivatives thereof as an anti-cataract agent.

Diethyldithiocarbamate (DDC) which is a reducing thiol derivative has been confirmed as an anti-cataract agent by the inventors.

As DDC is disadvantageously hydrophilic, it can not penetrate into the cornea and is not transferred to aqueous humor and the crystalline lens. In addition, DDC is also easily oxidized and unstable. Its bioavailability, therefore, is low and the anti-cataract activity of DDC can not be sufficiently expressed.

Now, it has been found that disulfide derivatives and sulfide derivatives of the reducing thiol derivatives, which are chemically stable and lipophilic and therefore can easily pass through the cornea, are useful as anti-cataract agents.

Thus, in the course of the reserch on some radical scavengers, which have high bioavailability and a stable reducing SH group, as anti-cataract agents, it has been found that Disulfiram (DSF, tetraethylthiuram disulfide, Antabuse) which has been used for many years in therapy for chronic alcoholism in the United States shows a potential anti-cataract effect. DSF is a dimer of DDC, of which administration methods and non-toxicity are already confirmed, and possesses significant potential anti-cataract effect when compared with DDC.

Since (1) DSF is able to pass through the cornea due to its fat-solubility and (2) it is known that one molecule of DSF produces two molecules of DDC by catalytically reductive action of albumin and one molecule from DDC binds to SH group of albumin and another molecule from DDC is released, DSF which has easily passed through the cornea seems to be converted to DDC by action of albumin in the cornea and the lens to present an anti-cataract effect therein.

The second object of the invention is to provide a pharmaceutical composition for treatment of cataract which comprises an anti-cataract agent and fine particles which enhance the bioavailability of anti-cataract agent and the transportation to the target positions.

That is, DSF is a lipophilic substance and therefore, its ability of penetrate into the cornea is very high. On the other hand, it is not miscible with water such as tear, and is very disadvantageously to be incorporated in an aqueous eye drop penetration. This problem was solved by microcapsulation of DSF as fine particles such as emulsions, nanocapsules, albumin microspheres and liposomes.

The third object of the invention is to provide a positively charged fine particle, which is used for transportation of anti-cataract agent into the aqueous humor and the lens.

That is, since the surface of the cornea is negatively charged, fine particles are treated with a positively charged substance to add a positive charge on the surface thereof. The fine particles thus treated, of which the charged surface is confirmed as positive by determination of $\zeta$ potential, can easily bind to the negatively charged cornea, whereby anti-cataract agent in the fine particles can be positively transferred into the aqueous humor and the lens. Thus the inventors have developed fine particles for anti-cataract agents with high bioavailability.

Therefore, the present invention provides; (1) a method for treatment of cataract which comprises administering to a subject in need of such treatment, a radical scavenger in an amount effective in treatment of cataract selected from the group consisting of a reducing thiol derivative, and a disulfide derivative or a sulfide derivative thereof, for example, compounds of formula (I) and (II), compounds of formula (III) or a cephem, and (2) a pharmaceutical composition for treatment of cataract which comprises an anti-cataract agent containing a radical scavenger, and fine particles, such as emulsions, nanocapsules, alubmin microspheres and liposomes, which carries the anti-cataract agent and has a lipophilic and positively charged phase on the surface thereof.

DETAILED DESCRIPTION OF THE INVENTION

The term "a reducing thiol derivative" includes compounds which are easily oxidized, for example, compounds of formula:

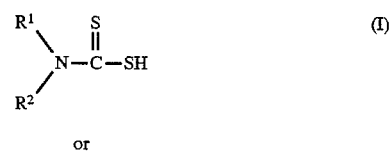

or

-continued

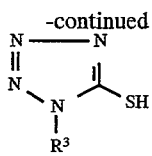
(II)

wherein $R^1$, $R^2$ and $R^3$ are independently a straight or branched lower alkyl which may be substituted by hydroxy, lower alkyloxy or lower alkyl carbonyloxy, their derivatives or a pharmaceutically acceptable salt thereof, preferably, diethyl dithiocarbamate, 1-methyl-1H-tetrazol-5-yl-thiol and 1-(2-hydroxyethyl)-1H-tetrazol-5-yl-thiol or a pharmaceutically acceptable salt thereof.

Examples of "a disulfide derivative" which is derived from reducing thiols are compounds of formula:

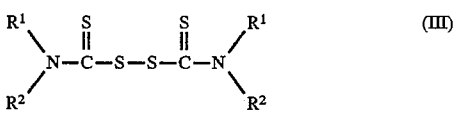
(III)

wherein $R^1$ and $R^2$ are as defined above, derivatives thereof and pharmaceutically acceptable salts thereof, preferably, DSF.

As examples of "a sulfide derivative" which is also derived from the reducing thiol derivatives, there can be mentioned cephems such as cefamandole, cefoperazone, cefmenoxime hemihydrochloride, cefmetazole, cefotetan, latamoxef, cefbuperazone, cefpiramide and flomoxef and pharmaceutically acceptable salts thereof which are the derivatives from 1-methyl-1H-tetrazol-5-yl-thio and 1-(2-hydroxyethyl)-1H-tetrazol-5-yl-thiol, preferably cefmetazole.

The term "Radical scavengers" which have high reactivities against radicals, and can react with radicals rapidly, and can remove radicals from the reaction system, and can terminate the subsequent reactions. More specifically, radical scavengers can trap the active oxygens such as singlet oxygen, hydroperoxide, superoxide anion and hydroxyl radical and suppress biological disorders by chain oxidation reactions related to these oxygens.

The term "treatment" includes the prevention of cataracts and cure of the disease.

The term "lower alkyl" in lower alkyloxy or lower alkyl carbonyloxy group includes saturated and straight or branched hydrocarbon groups having 1 to 6, preferably 1 to 5, more preferably, 1 to 4 atoms. For example, there can be mentioned methyl, ethyl, propyl, isopropyl, butyl and t-butyl.

Small particles such as liposomes, emulsions, nanocapsules and albumin microspheres are used as carriers for the anti-cataract agents.

Liposomes which are formed in water by dispersing natural lipids are similar to the structure of mammalian cell membranes and are used as a model of artificial cell membrane. Therefore, there are many suggestion in medical and pharmaceutical fields that liposomes used as tissue targeting drug carriers, artificial red blood cells, and cell-modifying and enzyme-immobilizing substrates have good adaptations to living bodies. However, while liposomes prepared by the ordinary methods have been applied to the purposes mentioned above, there were few preparations which could be used in practice. The reasons are for that firstly the liposomes prepared by the conventional method have less structural stability if they have good adaptation to tissues, and that secondly they did not have the for tissue and cell targeting which is very important factor for drug carriers.

Therefore, to improve their weak points we modified liposomes with lipophilic positively charged substances, and the liposomes were enhanced in their stability and targeting ability to objective tissues and cells.

Though the techniques for the addition of surface charge to liposomes have been available, the relationship between the added membrane charge and drug transport of liposomes has not been clarified quantitatively. In this invention, the relationship between membrane charge modified by lipophilic positive substances and stability of liposomes was proved by determination of $\zeta$-potential of liposomes and heat flow of liposomes by a differential scanning calorimetry. Then liposomes prepared by this manner which show the controlled release of drugs and can transfer the drugs to crystalline lens through cornea, can be used for treatment of cataracts.

Accordingly, the liposomes to which are added positive charge by the treatment of lipophilic positively charged substances and loaded anti-cataract agents, show cornea specific targeting and binding, good transability to transport drugs into cornea and, no toxicity against eye tissues. Therefore, it is suggested that the administration of this preparation is an effective way to cure cataracts.

In the present invention, small particle carriers such as said liposomes, emulsions, nanocapsules, and albumin microcapspheres which are applied to pharmaceutical technology, can be used for cure against cataracts.

Method for Preparation of Liposomes

A solution of vesicle-forming lipids in a solvent such as chloroform or ether in a round-bottomed flask is evaporated under nitrogen to form thin film of lipid on the inside wall of the round-bottomed flask. The dried film is hydrated by vortexing in water or buffers. Subsequently the resulting suspensions are sonicated using a probe for 1–3 min. The suspensions can be used as liposome preparations.

The preparation procedure of liposomes by the method of reverse-phase evaporation follows. Several phospholipids, either pure or mixed with other lipids such as cholesterol, long-chain alcohols etc., can be used with similar results. The lipid mixture is added to a round-bottom flask with long extension neck. The aqueous phase is added, the system is kept continuously under nitrogen, and the resulting two-phase system is sonicated briefly (a few minute) in a bath-type sonicator until the mixture becomes either a clear one-phase dispersion or a homogeneous opalescent dispersion. The mixture is then placed on an rotary evaporator and organic solvent is removed under reduced pressure. The obtained dispersions can be used as liposome preparations.

In either of the two methods mentioned above, hydrophilic and lipophilic agents used as anti-cataract drugs are dissolved in appropriate buffers and in organic solvents, respectively.

Other methods besides the above two methods, such as French-press method, freezed-dried method and freezed-thawed method can also be used for preparation of liposomes.

Liposomes presented in this patent can be prepared by conventional methods and those which have been reported already consist mainly of phospholipids and cholesterol. Phospholipids such as egg york lecithin, soybean lecithin, phosphatidylcholine, phosphatidylethanolamine, phosphatidylserine, phosphatidylinositol, phosphatidylglycerol, phosphatidic acid, and sphingomyelin etc., can be used for preparation of liposomes and liposomes can be prepared by using one or more combinations of these lipids.

Liposomes of the present invention consist at least of said lipids and an anti-cataract agent mentioned in sections following, and then an appropriate amount of cholesterol may be added to said lipids depending on the anti-cataract agent and lipophilic negatively or positively charged substances to be used, and cholesterol may be added advantageously when liposomes contain lipophilic negatively charge substances.

Method for Preparation of Emulsions

There are two types of emulsions i.e., water in oil (w/o) and oil in water (o/w) types which are determined by emulsifier used. Emulsions are formed as small vesicles by mixing of oil and water. For example w/o/w emulsions are prepared by the method of two step emulsifying which in a first step involves preparing w/o emulsions and in second step involved dispersing w/o emulsion it into water containing appropriate emulsifier.

Typical oil-in-water emulsions are prepared containing 10% (w/w) soybean oil, various concentrations (0.6–2.0% (w/w)) of egg lecithins (phospholipids), and 2.5% (w/w) glycerol in a sufficient amount of distilled water. The emulsifiers (egg lecithins) are dissolved in the oil phase, heated to 80° C. in a tank, and water which had been preheated to 80° C. is added to the solution. The agitator used is an autohomomixer, a high shear mixer; the temperature of the mixture is maintained at 80° C. for 30 min after the start of agitation in the tank. The impeller speed is kept at 10,000 rev/min. To make fine emulsions, coarse emulsions are introduced rapidly into a two-stage pressure homogenizer operating at 4500 psi. The obtained dispersions can be used as emulsion preparations.

Method for Preparation of Microcapsules

Microcapsules are prepared by coating the surface of small drug vesicles as core with polymers. Microcapsules are prepared by the method of coacervation and method of surface coagulation. In a coacervation method, core substances are dispersed in solution containing coating materials (polymers), and the surface of core is coagulated with coacervate, and the coagulate is hardened. Ethylcellulose, poly-lactate, polyvinylacetate, gelatin and starch etc. are used as coating materials for preparation of microcapsules.

Method for Preparation of Microspheres

The preparation of microcapsules mentioned above is one coating technique. On the other hand, microspheres are dispersed as solution or crystal of drugs in macromolecule matrix. Fundamentally microspheres are prepared by the method which comprises emulsifying of albumin solution in cotton oil or organic solvent (w/o emulsion) and hardening such as by heating, chemical bridging, drying in water, or polymerization by irradiation. Biodegradable polymers such as albumin, gelatin, dextran, polylactate, polyethylenecarbonate, and non-biodegradable polymers such as polystyrene, agarose, polyacrylamide etc. are used as matrix for the preparation of microspheres. The particle sizes of microspheres can be changed from 0.3 to 500 μm by using detergents.

Method for Preparation of Nanocapsules

Nanocapsules are small particles with nanometer order of diameter containing drugs. In the same way of microcapsules, nanocapsules can be prepared by the methods as coacervation and micelle coagulation using high molecular materials such as albumin, gelatin alkylcyanoacrylate.

Method for addition of Lipophilic Positive Charge into Small Particles

Addition of positive charge into small particles can be performed by mixing of lipophilic positively charged substances with membrane forming matrix when preparing small particles simultaneously or thereafter.

The lipophilic positively charged substances of the invention include cetylpyridinium chloride (CPC), dimethyldialkyl ($C_8$ to $C_{18}$) ammonium bromide (DC-1-8), N-methyl-N-(β-hydroxyethyl)-didodecyl ammonium bromide (DC-2-12), N-(α-trimethylammonioacetyl)-didodecyl-L-glutamate chloride (DC-3-12L), N-(α-trimethylammonioacetyl)-didodecyl-D-glutamate chloride (DC-3-12L), N-(α-trimethylammonioacetyl)-O,O'-bis-(1H, 1H, 2H, 2H-perfluorododecyl)-L-glutamate chloride (DC-5-8F2L), and as amine salts of cationic detergents can be mentioned, for example, alkyl amine salts, polyamine and alkanol amine fatty acid derivatives, alkyl quartenary ammonium salts such as alkyl trimethyl ammonium salts, dialkyl trimethyl ammonium salts and alkyl dimethyl benzyl ammonium salts, cyclic quartenary ammonium salts such as alkyl pyridinium salts and alkyl isoquinolinium salts, aromatic ammonium salts such as benzethonium chloride, and nitrogen containing detergents including, for example, polyoxyethylene fatty acid amide, polyoxyethylene alkyl amine, alkylol amide, and alkylamine oxide.

The lipophilic positively charged substance is added, for example, in an amount of 1 to 30% by mole, preferably 3 to 20% by mole, most preferably 5 to 15% by mole based on the total fine particles components.

The lipophilic and positively charged fine particles containing anti-cataract agent of the present invention, which are prepared by the method mentioned above, are used for preparing aqueous eye drops, aqeous suspensions for eye drops, non-aqueous eye drops, non-aqeous suspensions for eye drops or eye ointments by conventional processes.

A unit dose depends on the severity of conditions of cataract and body weight or age of patients and like. Due to the low toxicity of the radical scavenger of the invention, the unit dose is not limited and preferably is 1 μg to 1 mg and preferably a dose per day is 1 μg to 50 mg.

BRIEF DESCRIPTION OF THE DRAWINGS

FIGS. 10A and 10B show anterior (FIG. 10A) and nuclear opacity (FIG. 10B) in crystalline lens of X-irradiated rats treated with or without anti-cataract agents.

FIG. 11 shows posterior opacity in crystalline lenses of X-irradiated rats treated with or without anti-cataract agents.

FIGS. 17A and 17B show opacity (slit image, FIG. 17A) and transparency (retroillumination image, FIG. 17B) in crystalline lenses of selenite rats treated with or without anti-cataract agents.

EXAMPLE

Example 1

Figure 1A:
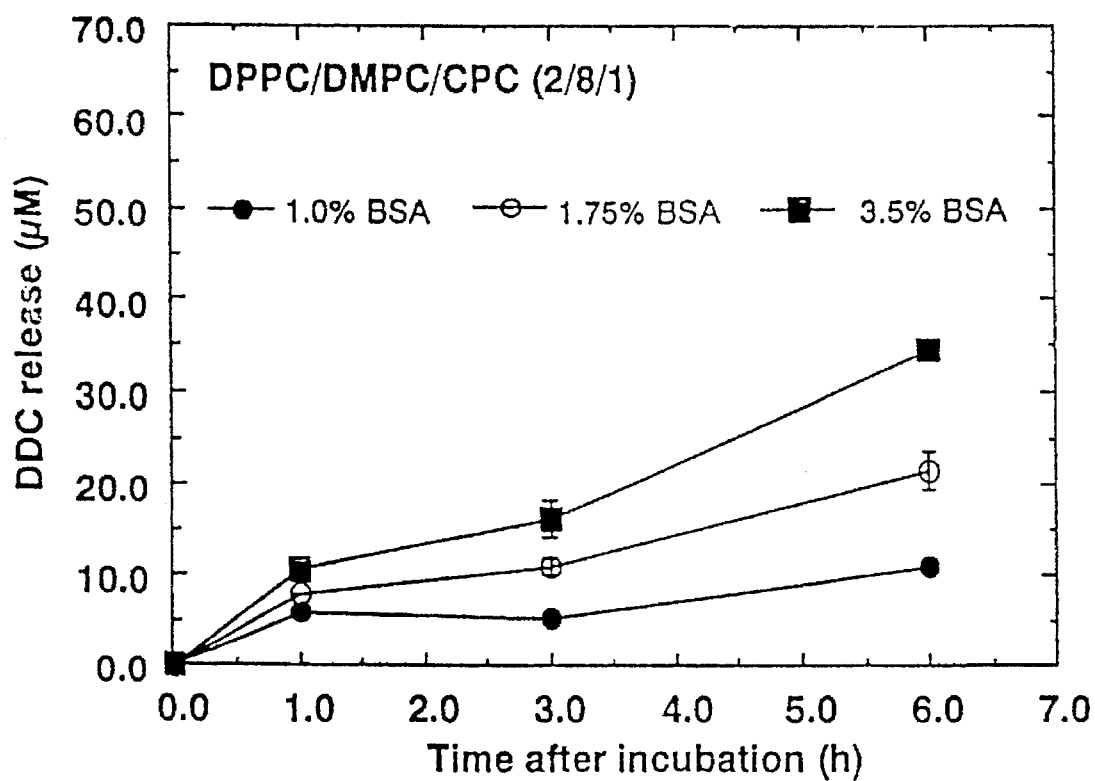
FIGS. 1A and 1B show DDC release from liposomes containing DSF at pH 8.0.

Method for Preparation of Liposomes Containing DSF

Liposomes containing DSF were prepared by the method of reverse phase solvent evaporation with a minor modification. DSF 10 mg, DPPC, DMPC and CPC were dissolved in 20 ml of dichloromethane and this solution was used as a hydrophobic phase. The hydrophobic phase was mixed with 10 ml of buffer solutions (A: Hind-Goyan's buffer, pH 6.5; B: Gifford's buffer, pH 8.0) and was sonicated under stream of nitrogen gas by using a bath type sonicator (Branson Cleaning Equipment Company, U.S.A). The w/o emulsion was aspirated for 30 min at 37° C. to remove $CH_2Cl_2$. The Liposomes were passed through an Excluder with membranes (pore sizes of 1.0, 0.6, 0.2 and 0.1 µm), which repeated ten times for each membrane. The particle size of obtained liposomes was about 80 nm.

Preparation Method of Liposomes Containing Cefmetasol (CMZ)

Liposomes containing CMZ was prepared by the method mentioned above except of using CMZ dissolved in buffer solutions. DPPC, DMPC and CPC were dissolved in 20 ml of dichloromethane and this solution was used as a lipophilic phase. The lipophilic phase was mixed with 10 ml of CMZ solution (1.0 g/ml) dissolved in buffer solutions (A: Hind-Goyan's buffer, pH 6.5; B: Gifford's buffer, pH 8.0) and was sonicated under stream of nitrogen gas by using a bath type sonicator. The w/o emulsion was aspirated for 30 min at 37° C. to remove $CH_2Cl_2$. The Liposomes were passed through an Excluder with membranes (pore sizes of 1.0, 0.6, 0.2 and 0.1 µm), which repeated ten times for each membrane. To separate the liposomes from unencapsulated CMZ, the liposomes were chromatographed on a column Superose 6 (Pharmacia LKB Biotechnology AB, Sweden) equilibrated with 10 mM sodium phosphate buffer (pH 7.4) containing 145 mM NaCl and 1 mM EDTA. The white turbid fractions were collected and used as a CMZ-liposome preparation. The particle size of obtained liposomes was about 100 nm.

Determination of Encapsulation of DSF in Liposomes

The determination of DSF content loaded in the liposomes was carried out by following. Methanol was added to the liposomes obtained to disrupt the lipid membrane, and then it was mixed with an internal standard solution and injected into HPLC apparatus. The liposomes were diluted by 4 volumes of buffers such as Hind-Goyan's buffer (pH 6.5) and Giford's buffer (pH 8.0) and ultrafiltrated by using a Centrisert II. DSF in filtrate without liposomes was assayed by HPLC. However, no DSF in the solution was measured and it was found that all of the drug added was incorporated in liposome membranes.

Encapsulation Percentage of DSF-Liposomes

The encapsulation percentages of DSF in DSF-liposomes consisted of various lipid compositions was shown in Table 1. Encapsulation percentage of DSF in all liposomes shown in Table 1 were more than 90%.

TABLE I

Lipid Compositions and Encapsulation Percent of Liposomes Containing DSF

| Liposomes | Content (mg/10 ml) | | | Encapsulation (%) | ζ-Potential (mV) |
|---|---|---|---|---|---|
| | DPPC | DMPC | CPC | | |
| Dispersion in buffer (pH 6.5) | | | | | |
| DPPC/DMPC (5/5) | 250 | 231 | — | 94.4 | −13.47 |
| DPPC/DMPC/CPC (5/5/1) | 250 | 231 | 24.7 | 96.3 | 41.40 |
| DPPC/DMPC/CPC (2/8/1) | 90 | 336 | 22.1 | 100.7 | 48.12 |
| Dispersion in buffer (pH 8.0) | | | | | |
| DPPC/DMPC/CPC (5/6/1) | 250 | 231 | 24.7 | 92.0 | — |
| DPPC/DMPC/CPC (2/8/1) | 90 | 336 | 22.1 | 99.1 | — |

DPPC: dipalmitoyl phosphatidylcholine, DMPC: dimyristoyl phosphatidylcholine, CPC: cetylpyridinum chloride.

ζ-Potential of Liposomes Containing DSF

ζ-Potential of liposomes containing DSF was determined by using a Lazar Zee Meter Model 501 (Pen Kem Comp., Ltd., USA). The liposomes were diluted by 150 volumes of 5 mM potassium phosphate buffer (pH 6.5) and its ζ-potential was determined at 150 V. The ζ-potential was corrected for change of temperature by following a equation.

ζ-potential (corrected)=ζ-potential (determined)×(1−0.027)

CPC in liposomes was added for enhancement of positive charge on surface of liposome membrane. The addition of one molar ratio of CPC against lipids rose to 40–50 mV from about −13 mV (liposomes without CPC).

Determination of DDC Release from Liposomes Containing DSF

The reaction mixture consisted of 0.24 ml of liposomes containing DSF diluted 2.5-fold with Gifford's buffer (pH 9.5, 8.0 and 6.5) and 0.25 ml of bovine serum albumin (BSA) solution (1–7%) in same buffers. The reaction was performed at 35° C. for 0–6 hr and terminated by cooling in the ice bath for 3 min. The reaction mixture was ultrafiltrated by using Centrisart II (Sartorius AG, Germany) and the filtrate was used as a sample for HPLC.

DDC Release from Liposomes Containing DSF (1) Release in Gifford buffer (pH 8.0)

Figure 1B:
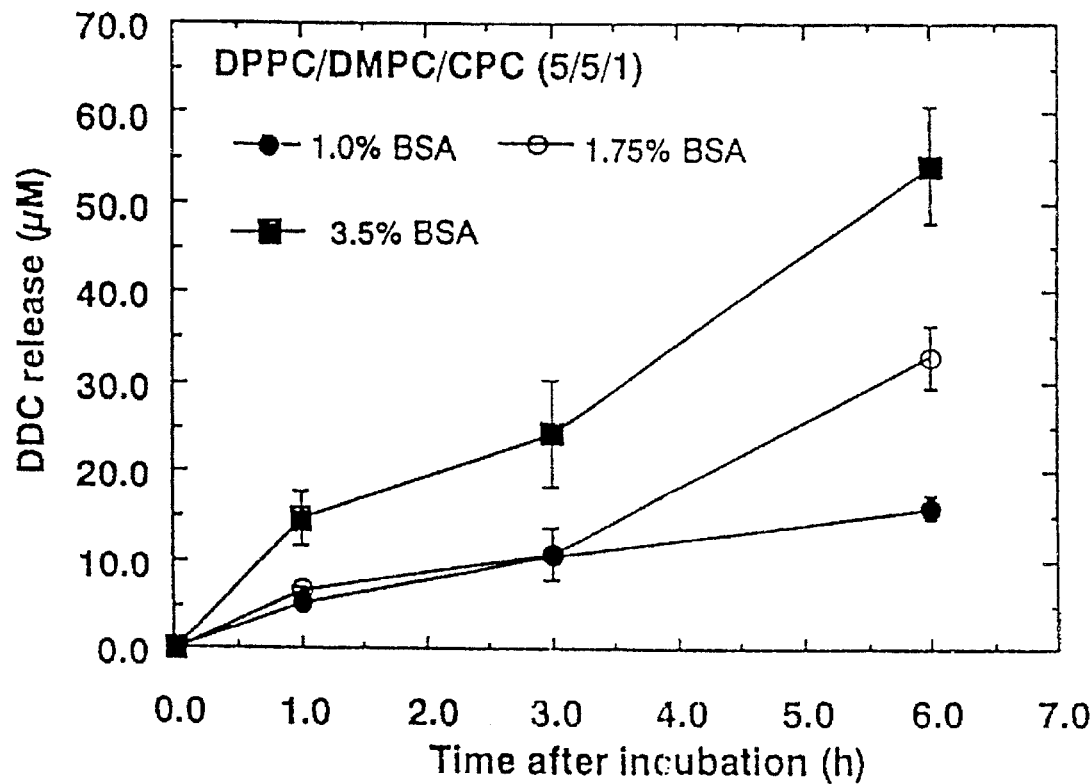

FIGS. 1A and 1B show DDC release profiles from the liposomes in 3 different concentrations of BSA solutions, 1.0, 1.75, and 3.5%, at pH 8.0 by using Centrisart II which includes membrane to separate the DDC released from the liposomes in the incubation mixture. DPPC/DMPC/CPC (5/5/1, molar ratio) liposomes had a higher CDDC release rate than DPPC/DMPC/CPC (2/8/1) liposomes (FIG. 1).

(2) Release in Hind-Goyan's buffer (pH 6.5)

No DDC release from all liposomes tested was observed at pH 6.5.

Experiment of In Vitro Transcorneal Penetration

Figure 2:
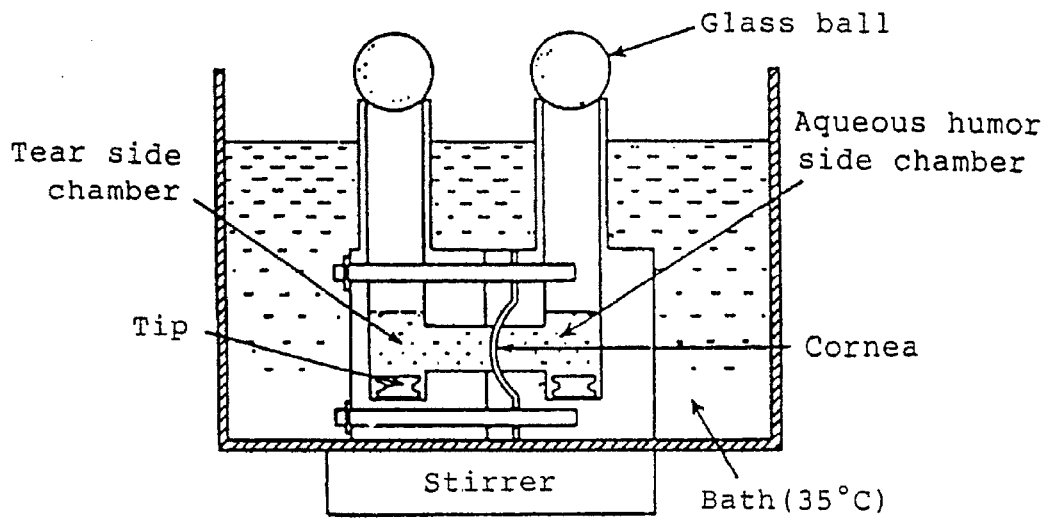
FIG. 2 shows an experimental device for cornea transpenetration.

Male rabbit, 2.0 kg of body weight was sacrificed by a injection of lethal dose of pentobarbital into a car vein and then two eyeballs were removed from cash rabbit. The cornea was set to the cell in which donor side was filled with liposomes containing DSF and in reservoir side with 10 mM HEPES buffer (pH 7.4) containing 136 mM NaCl, 5.3 mM KCl, 1.0 mM $K_2HPO_4$, 1.7 mM $CaCl_2$ and 5.5 mM glucose, shown in FIG. 2. The penetration was carried out at 37° C. for 0–6 hr. The sample (50 μl) was withdrawn from reservoir side at the indicated times. DDC in the sample was determined by the HPLC method (FIG. 2).

In Vitro Transcorneal Penetration of DDC from Liposomes Through Rabbit Cornea (1) Penetration at pH 8.0

Figure 3:
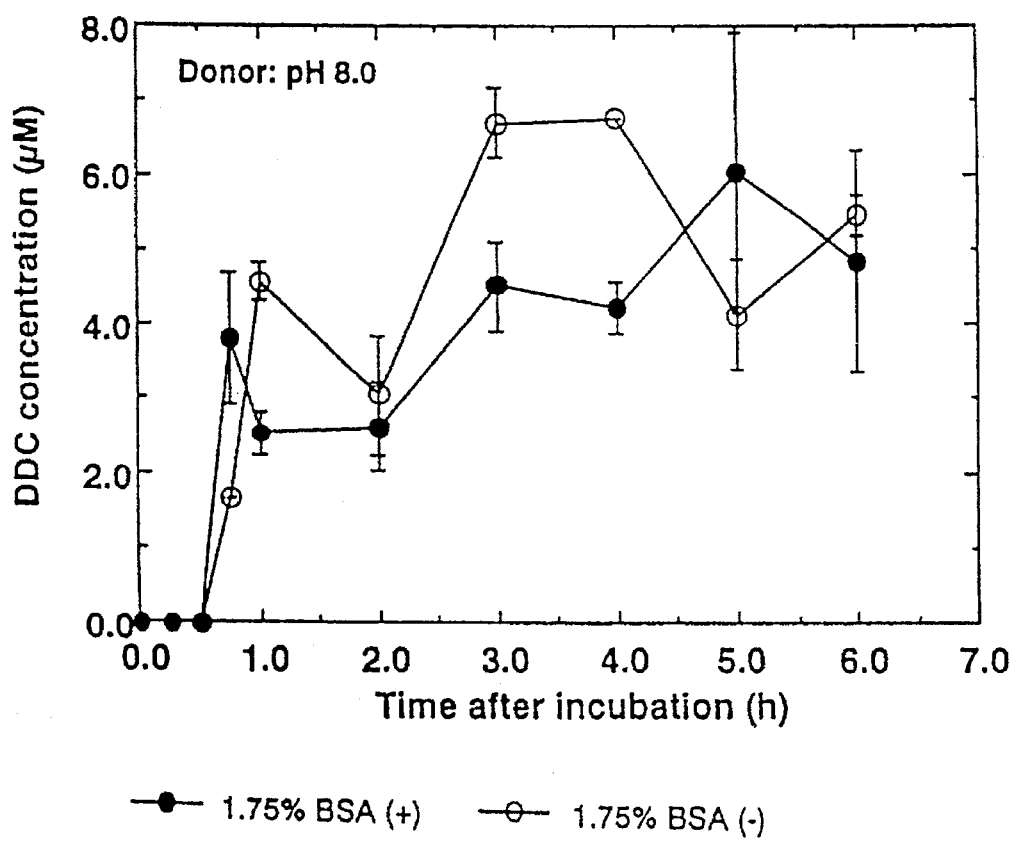
FIG. 3. shows penetration of DDC releasing from DPPC/DMPC/CPC (2/8/1) liposomes containing DSF through a rabbit cornea.

FIG. 3 shows DDC penetration profiles through rabbit corneas at pH 8.0 About one-half hour after incubation, DDC from the liposomes was observed in the reservoir solution. Addition of 1.75% BSA in donor solution did affect on the DDC penetration (FIG. 3).

(2) Penetration at pH 6.5

Figure 4:
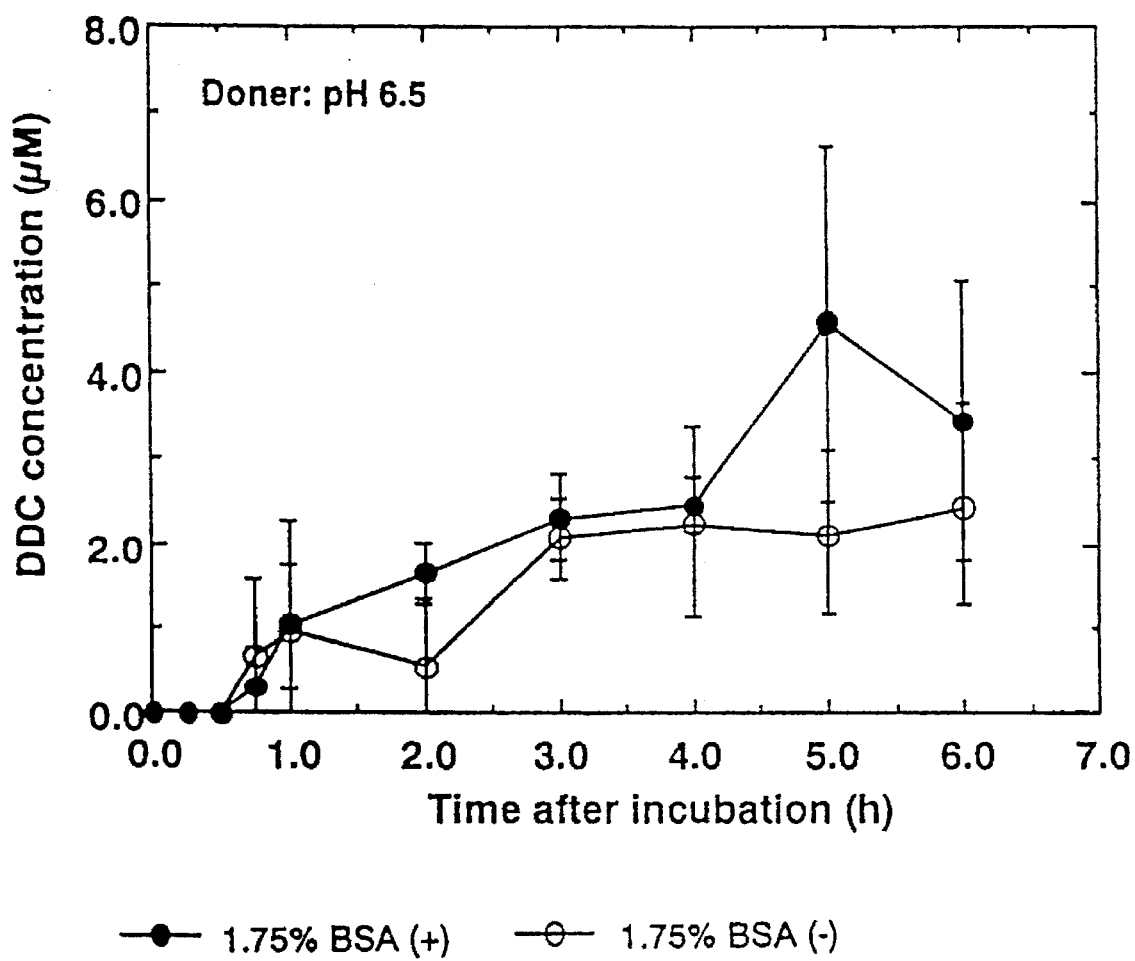
FIG. 4 shows penetration of DDC releasing from DPPC/DMPC/CPC (2/8/1) liposomes containing DSF through rabbit cornea.

FIG. 4 shows the DDC penetration profiles at pH 6.5. Six hours after incubation, DDC content in the reservoir solution was one third of that at pH 8.0 (FIG. 4).

Example 2

Procedure Using Microspheres Containing DSF Using Copoly (Lactic/Glycolic) acid (LGA)

LGA-7515 (Wako Pure Chemical Industries, Ltd.) microspheres containing DSF were prepared by an in-water drying method. One hundred milligram of DSF, 850 mg of LGA-7515 and 50 mg of CPC were dissolved in 12 ml of methylene chloride. The solution was then poured into 150 ml of 0.5% (w/v) polyvinyl alcohol solution under stirring at 800 rpm by means of magnetic stirrer. The stirring continued for 2 hr at 25±2° C. to evaporate off methylene chloride. The microspheres were passed through stainless steel sieves (mesh size: 297, 177, and 75 μm). The microspheres were collected by filtration through a stirred glass disk, washed with purified water, and dried under reduced pressure at room temperature. The encapsulation percent of DSF in the microspheres was about 90% and its diameter was 1.0±0.3 μm.

Example 3

Procedure of Albumin Microspheres Containing DSF

Fine power (250 mg) of DSF was suspended in solution of bovine serum albumin (250 mg/ml of purified water). The suspension was added into 100 ml of cotton oil containing 10 (v/v) % Span 85, and stirred for 10 min at 250 rpm by glass stirrer, and emulsified by a Sonicator, Shimadzu USP-600 (100 w, 30 min). This micro-emulsion (w/o type) was added into a bath containing glycerine at 100° C. and then microsphere was formed. Subsequently this microsphere was washed of glycerine by organic solvents such as ether etc. Encapsulation percent of DSF in the microsphere obtained was about 95%. Average particle size of this microsphere was 1±0.5 μm.

Example 4

Pharmaceutical Preparations

The liposomes containing DSF prepared by the method of Experiment 1 or those diluted with solutions containing preservatives and tonicity agents were used as eye drop preparations.

Determination of In Vitro Anti-Cataract Activities of Various Agents (1) Method Male ddY mice, 6 weeks old, were killed by decapitation, and the globes were excised. The lenses were removed by a posterior approach and then transferred on a nylon net to an petri containing D-MEM medium (low glucose). The lenses were incubated at 37° C. for 2 hr and clear transparent lenses were collected to be used for following experiments. The lenses were incubated at 37° C. for 1.5 hr in 3 ml of isotonic HEPES buffer (10 mM hepes, 139 mM NaCl, 5.4 mM KCl, 1 mM $K_2HPO_4$, 1.7 mM $CaCl_2$—$H_2O$, pH 7.4) containing 1 mM diamide. Those were transferred to an incubation test tube containing 3 ml of isotonic HEPES buffer (pH 7.4) containing 5.5 mM glucose with 1 mM DDC or GE (glutathione isopropyl ester). The diamide treated and non-treated controls were treated by the 5 hr-incubation without the above agents. The wet weight of these treated lenses were determined.

(2) Determination of GSH in Mice Lenses

The treated lenses were homogenized with 0.5 ml of purified water by Teflon homogenizer. GSH in the homogenate was determined by the method of Beutler using DTNB and the HPLC method followed.

Fifty microliter of the lens homogenate were added into 100 µl of acetonitrile containing 100 µg of sodium pantothenate (internal standard) and centrifuged at 12,000 rpm for 10 min. The supernatant solution (10 µl) was injected into a HPLC apparatus, Shimadzu LC-10AD equipped with a column oven, CTO-6A and the chromatography were performed under the conditions: a column of Supersphere 100RP-18 (particle size: 4 µm, column size: 4.0×250 mm), mobile phase of 5% methanol containing 1.0% TFA, flow rate of 1 ml/min, and column temperature at 35° C.

(3) Effect of DDC and GE on GSH Content in Diamide Treated Lens

Figure 5:
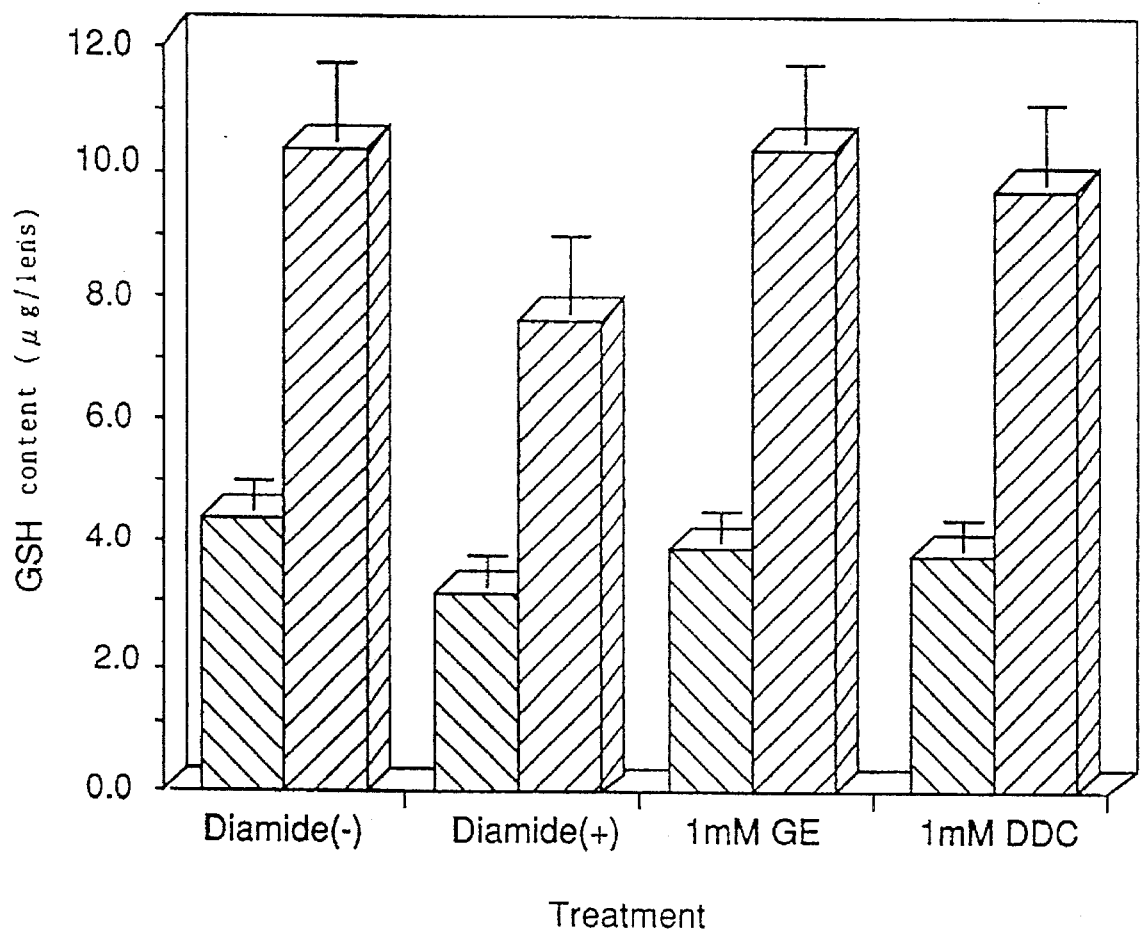
FIG. 5 shows effect of GE and DDC on GSH content in mouse crystalline lens treated with Diamide.

GSH contents in the treated lenses determined by DTNB method were shown in Table 2 and FIG. 5.

TABLE 2

Effect of Anti-Cataract Agents on GSH Contents in Diamide-Treatment Mice Lenses (DTNB Method)

| | GSH content (µg/lens) | Deviation |
|---|---|---|
| Contol | 10.3 | 0.5 |
| Diamide treatment | | |
| None | 7.6 | 0.3 |
| 1 mM GE | 10.3 | 0.8 |
| 1 mM DDC-NA | 9.8 | 0.8 |

The GSH contents were 10.3±0.5 µg/lens in non-treated lenses and 7.3 µg/lens in diamide-treated lenses. Diamide caused a rapid oxidation of lens GSH. By the diamide treatment there was a 30 percent decrease in total GSH. On the other hand, total GSH in lenses treated with 1 mM DDC and GE were restored by the control GSH level (FIG. 5).

GSH contents in the treated lenses determined by HPLC method are shown in Table 3 and FIG. 5.

TABLE 3

Effect of Anti-Cataract Agents on GSH Contents in Diamide-Treatment Mice Lenses (HPLC Method)

| | GSH content (µg/lens) | Deviation |
|---|---|---|
| Control | 4.4 | 0.3 |
| Diamide treatment | | |
| None | 3.1 | 0.2 |
| 1 mM GE | 4.0 | 0.2 |
| 1 mM DDC-NA | 3.9 | 0.4 |

All of data were about half of those obtained by DTNB method. However, restoring of GSH by the treatment of DDC and GE were observed by this method also (FIG. 5)

Effect of DDC and GE on $Na^+/K^+$ Ratio and $Ca^{2+}$ Contents in Diamide-Treated Mice Lenses (1) Methods Male ddY mice, 6 weeks old, were killed by decapitation, and the gloves were excised. The lenses were removed by a posterior approach and then transferred on a nylon net to a petri dish containing D-MEM medium (low glucose). The lenses were incubated at 37° C. for 19–20 hr in $CO_2$ incubator under 5% $CO_2$-air and clear transparent lenses were collected to be used for following experiments. The lenses were incubated at 37° C. for 1.5 hr in 3 ml of isotonic HEPES buffer (10 mM HEPES, 136.2 mM NaCl, 5.3 mM KCl, 1.0 mM $K_2HPO_4$, 1.7 mM $CaCl_2 \cdot 2H_2O$, 5.5 mM glucose pH 7.4) containing 1 mM diamide and the HEPES buffer without glucose. Those were transferred to an incubation test tube containing 3 ml of isotonic HEPES buffer (pH 7.4) with 1 mM DDC or GE. The diamide treated and non-treated controls were treated by the 5 hr-incubation without the above agents. The wet weight of these treated lenses were determined. Lenses were dried in vacuo at 100° C. for 8 hr, and then digested in 60% nitric acid (100 µl/lens) at 80° C. to degrade organic substances. One milliliter of purified water was added to the digests, and centrifuged at 300 xg for 10 min. Two tenth ml of the supernatant was mixed with 2 ml of purified water, and was used for measurement of $Na^{3o}$ and $K^+$. One tenth milliliter of 100 µg/ml lanthanum chloride was added to the residual supernatant and used for measurement of $Ca^{2+}$, $Na^+$, $K^+$ and $Ca^{2+}$ contents in the lenses were determined by atomic absorption spectrometer (Hitachi 180-80, Tokyo, Japan).

Effects of DDC and GE on $Na^+/K^+$ Ratio and $Ca^{2+}$ Contents in Diamide-Treated Mice Lenses

TABLE 4

| | Contents (mmol/kg of $H_2O$) | | | |
|---|---|---|---|---|
| | $Na^+$ | $K^+$ | $Ca^{2+}$ | Na/K ratio |
| Diamide (−) | 22.03 ± 3.39 | 95.90 ± 3.49 | 1.20 ± 0.27 | 0.23 ± 0.04 |
| Diamide (+) | 60.38 ± 13.49 | 61.29 ± 13.78 | 1.98 ± 0.27 | 1.11 ± 0.04 |
| DDC-Na | 36.56 ± 4.38 | 86.25 ± 4.02 | 1.09 ± 0.33 | 0.43 ± 0.07 |
| GE | 51.60 ± 9.57 | 79.67 ± 8.63 | 1.39 ± 0.30 | 0.67 ± 0.20 |
| CMZ | 40.59 ± 10.16 | 84.91 ± 10.06 | 1.11 ± 0.36 | 0.50 ± 0.19 |

Figure 6:
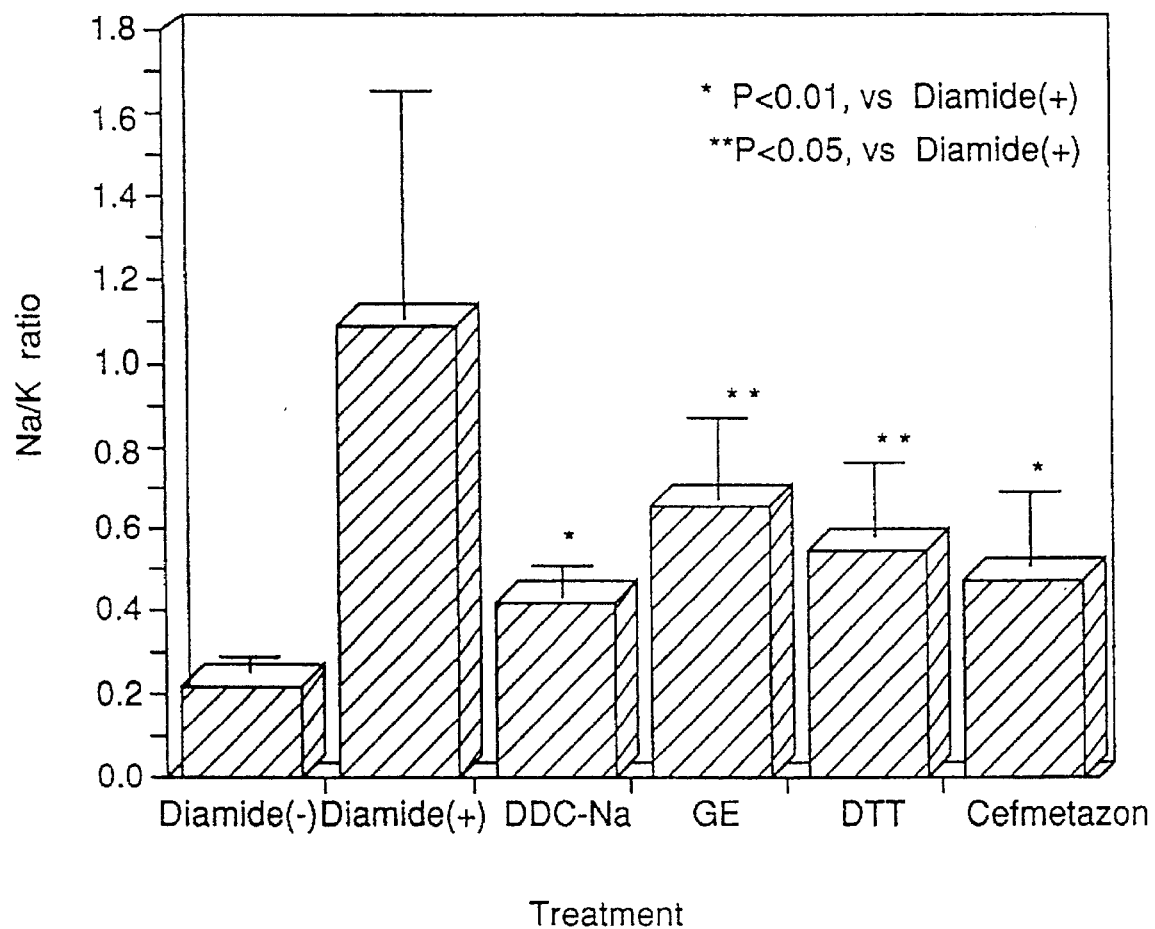
FIG. 6 shows changes of Na/K ratio in mice crystalline lenses treated with or without anti-cataract agents.
Figure 7:
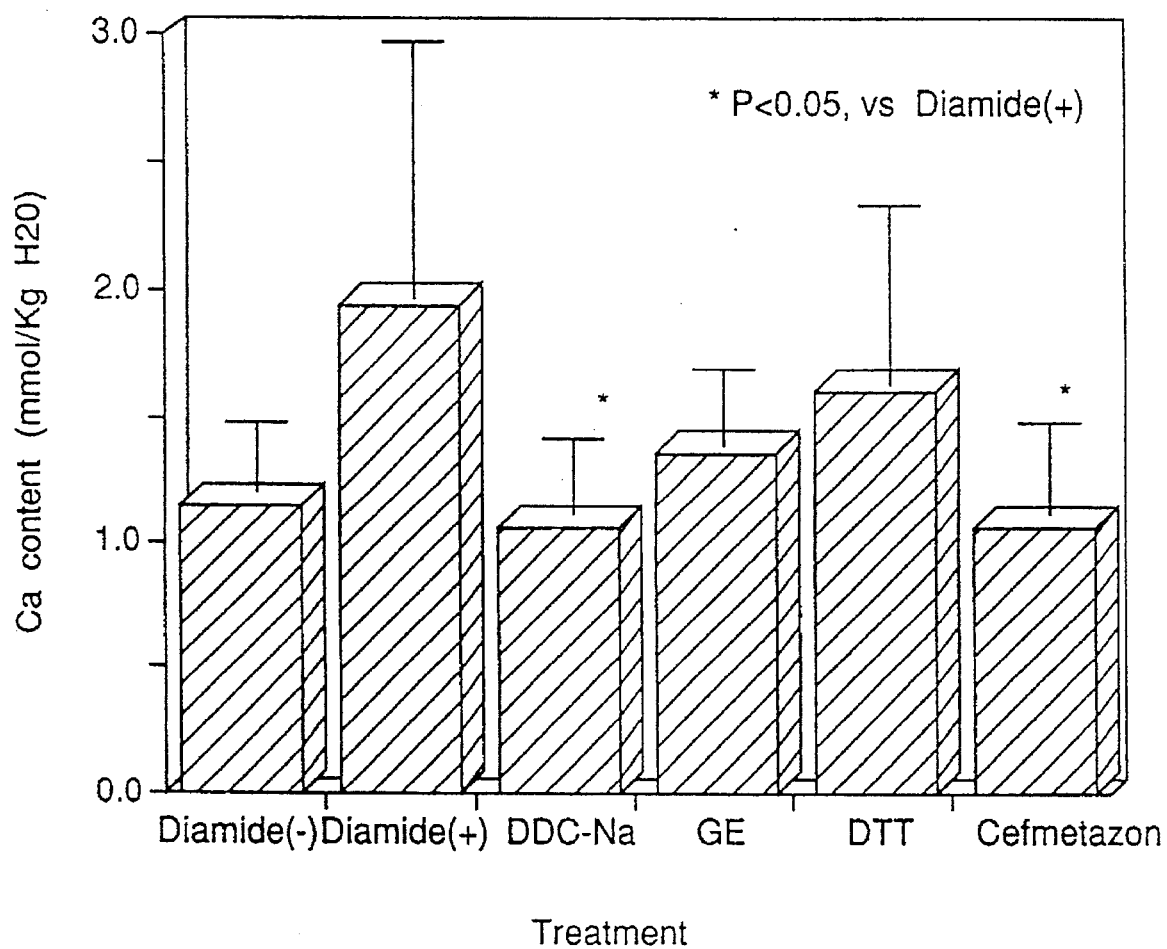
FIG. 7 shows changes of Ca contents in mice crystalline lenses treated with or without anti-cataract agents.

Effects of various agents on $Na^{3o}/K^+$ ratio and $Ca^{2+}$ contents in diamide-treated mice lenses are shown in Table 4 and FIG. 6. The treatments of 1 Mm DDC, GE, DTT and CMZ restored completely the $Na^+/K^+$ ratio and $Ca^{2+}$ content to the control levels (FIG. 6).

Inhibitory Activities of Various Agents Against Rat Lens Aldose Reductase (1) Methods Aldose reductase was prepared from rat lenses in the following manner. Lenses (20 to 30) were homogenized in 20 volumes of 5 mM sodium phosphate buffer (pH 7.4), followed by centrifugation at 18,000 xg for 5 min to remove insoluble materials. Solid ammonium sulfate was added to the supernatant fluid to 30% saturation. The suspension was centrifuged at 18,000 xg for 10 min and the supernatant was recovered. Aldose reductase was precipitated from 30% saturated solution by the addition of solid ammonium sulfate to 75% saturation, and obtained by centrifugation. The precipitate was collected and suspended in 3.2M ammonium sulfate.

The enzyme solution was assayed by following the absorbance at 340 nm on a Shimadzu UV-2000 spectrophotometer equipped with a temperature-controlled cuvette chamber. The solution (0.1 ml) was added to a cuvette containing phosphate buffer (1.6 ml, pH 6.2, 0.1M final concentration) and NADPH (0.1 ml, 0.25 mM final concentration), and the cuvette was inserted into the spectrophotometer. The reaction was started by the addition of DL-glyceraldehyde (0.1 ml, 50 mM final concentration) to the cuvette, and the decrease of absorbance at 340 nm for 5 min at 25° C. was measured. The reaction was linear for at least 8 min. Agents to be tested were dissolved with a minimal amount of dimethylsulfoxide and diluted to the desired concentration with purified water. The resulting solution (0.1 ml) was added to the cuvette. The reference blank (to correct for non-specific oxidation of NADPH and absorption of the agents) was prepared by using water instead of DL-glyceraldehyde solution.

(2) Results

Figure 8:
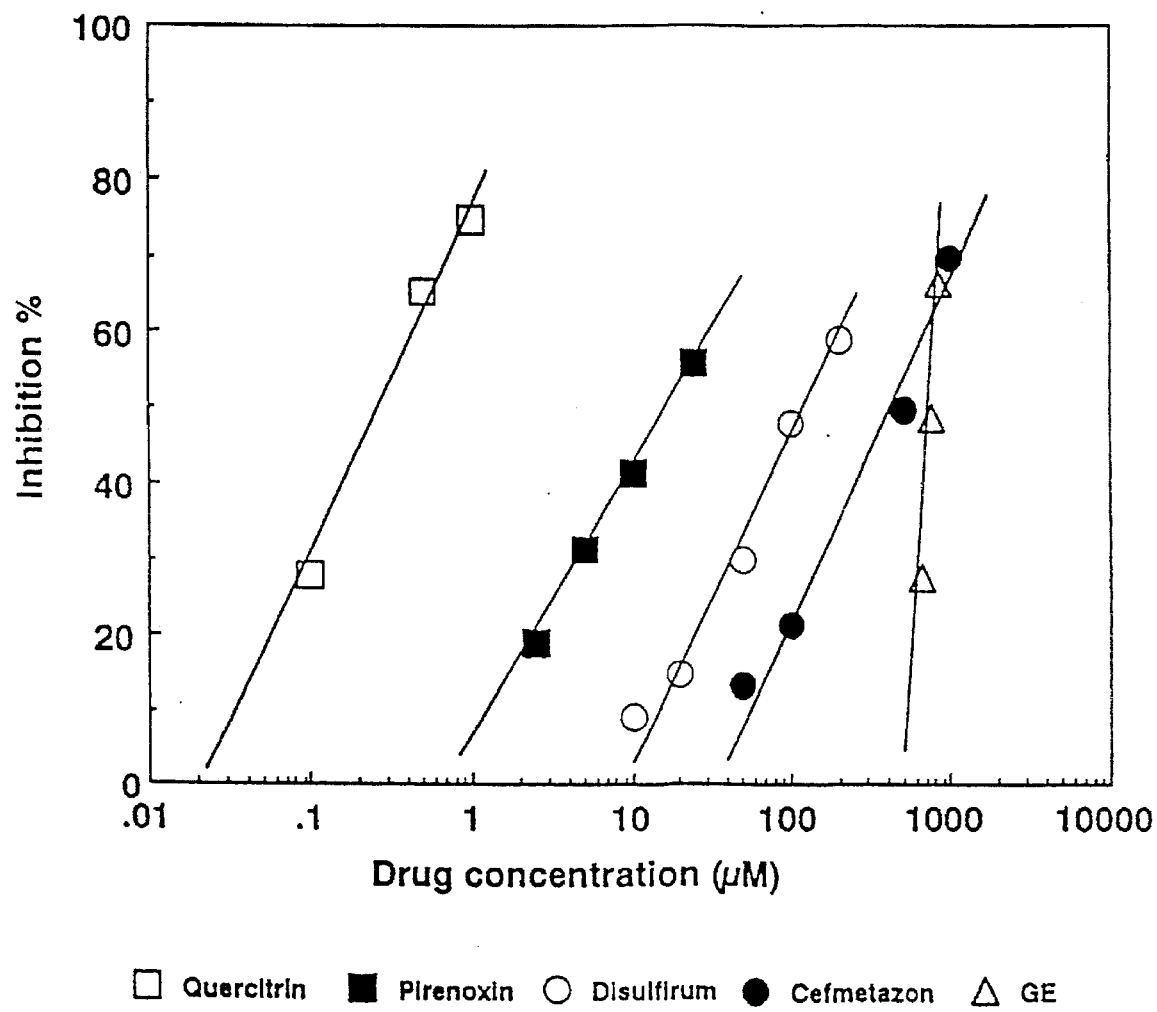
FIG. 8 shows inhibition activity of various drugs against aldose reductase from rat crystalline lens.

Inhibitory activities of various agents against rat lens aldose reductase are shown in Table 5 and FIG. 8. Quersitrine, pirenoxine, DSF, CMZ and GE showed lower inhibitory activities and trace or no inhibitory activity was observed in other agents (Table 5 and FIG. 8).

TABLE V

Inhibitory Activities ($IC_{50}$) of Anti-Cataract Agents against Aldose Reductase from Rat Crystalline Lens

| Agent | Range of concentration | $IC_{50}$ (µM) |
| --- | --- | --- |
| Quercitrin | 0.1–1.0 µM | 0.26 |
| Pirenoxine (Catalin) | 2.5–25 µM | 17.5 |
| Disulfirum (DSF) | 10–200 µM | 120 |
| Cefmetazon (CMZ) | 0.05–1.00 mM | 450 |
| Glutathione isopropyl ester (GE) | 0.65–0.85 mM | 760 |
| Frusultiamine (Alinamine F) | 0.13–1.25 mM | $1.00 \times 10^3$ |
| Tiopronin | 0.50–2.00 mM | $1.35 \times 10^3$ |
| Captopril | 0.50–2.00 mM | $1.45 \times 10^3$ |
| Glutathione (GSH) | 0.5–2.00 mM | $1.55 \times 10^3$ |
| Sodium diethyldithiocarbamate (DDC—Na) | 0.5–2.00 mM | $2.60 \times 10^3$ |
| Glutathione disulfide (GSSG) | 0.5–2.00 mM | $3.00 \times 10^3$ |
| Thiamine hydrochloride | 0.13–0.63 mM | N.D. |
| S-Methyl glutathione | 1.00 mM | N.D. |
| S-Ethyl glutathione | 1.00 mM | N.D. |
| S-Butyl glutathione | 0.05 mM | N.D. |
| S-(n-Propyl) glutathione | 0.05 mM | N.D. |

In Vivo Anti-Cataract Experiment of DSF-Liposomes Using X-Irradiated Rats

In this in vivo anti-cataract experiment, the liposomes prepared by the method of Experiment 1 was used. It was well known that the course of development of X-ray induced cataracts are similar to that of human senile cataract.

(1) Materials and Method

A. X-irradiation to Rats

The lenses of male Brown Norway Rats, 9 weeks old, was chosen as the experimental model. Both eyes of each animal were irradiated at 10 Gy by using a dose of 200 kVp X-rats, filtered with 0.5 mm Cu and 0.5 mm Al (HVL=1 mm of Cu). The animal bodies except the head was sealed with a lead sheet (1 mm of thickness) for avoiding its systemic disorder by X-ray.

B. Instillation of Drugs

Each 10 µl of liposomes containing DSF (1 mg/ml), DDC solution (1 mg/ml), GE solution (2 mg/ml) and CMZ solution (2.5 mg/ml) was instilled 3 times per day to both eyes of the rats which were one month after X-irradiation. The instillation was carried out for 6 months and the image analysis for anterior eye of rats was performed at monthly intervals by Nidek EAS-1000 Sheimpflug camera.

C. Image Analysis

Opacities of lenses of X-ray cataracts were digitized from the data of densitometry integrated area of the Scheimpflug images and were divided into 3 parts which were anterior, nuclear and posterior potions. Transparencies of the lenses were digitized from the data of the retroillumination images.

D. Determination of GSH in Rat Lenses

The treated lenses were homogenized with 0.5 ml of purified water by Teflon homogenizer. GSH in the homogenate was determined by the HPLC method followed.

Fifty microliter of the lens homogenate were added into 100 µl of acetonitrile 100 µg of sodium pantothenate (internal standard) and centrifuged at 12,000 rpm for 10 min. The supernatant solution (10 µl) was injected into a HPLC apparatus, Shimadzu LC-10AD equipped with a column oven, CTO-6A and the chromatography were performed under the conditions: A column of Supersphere 100RP-18 (particle size: 4 µm, column size: 4.0×250 mm), mobile phase of 5% methanol containing 1.0% TFA, flow rate of 1 ml/min, and column temperature at 35° C.

E. Determination of $Na^+$, $K^+$ and $Ca^{2+}$ in Rat Lenses

Lenses were dried in vacuo at 100° C. for 8 hr, and then digested in 60% nitric acid (100 µl/lens) at 80° C. to degrade organic substances. One milliliter of purified water was added to the digests, and centrifuged at 3000 xg for 10 min. Two tenth ml of the supernatant was mixed with 2 ml of purified water, and was used for measurement of $Na^+$ and $K^+$. One tenth milliliter of 100 µg/ml lanthanum chloride was added to the residual supernatant and used for measurement of $Ca^{2+}$, $Na^+$, $K^+$ and $Ca^{2+}$ contents in the lenses were determined by atomic absorption spectrometer (Hitachi 180-80, Tokyo, Japan).

(2) Results

Figure 9:
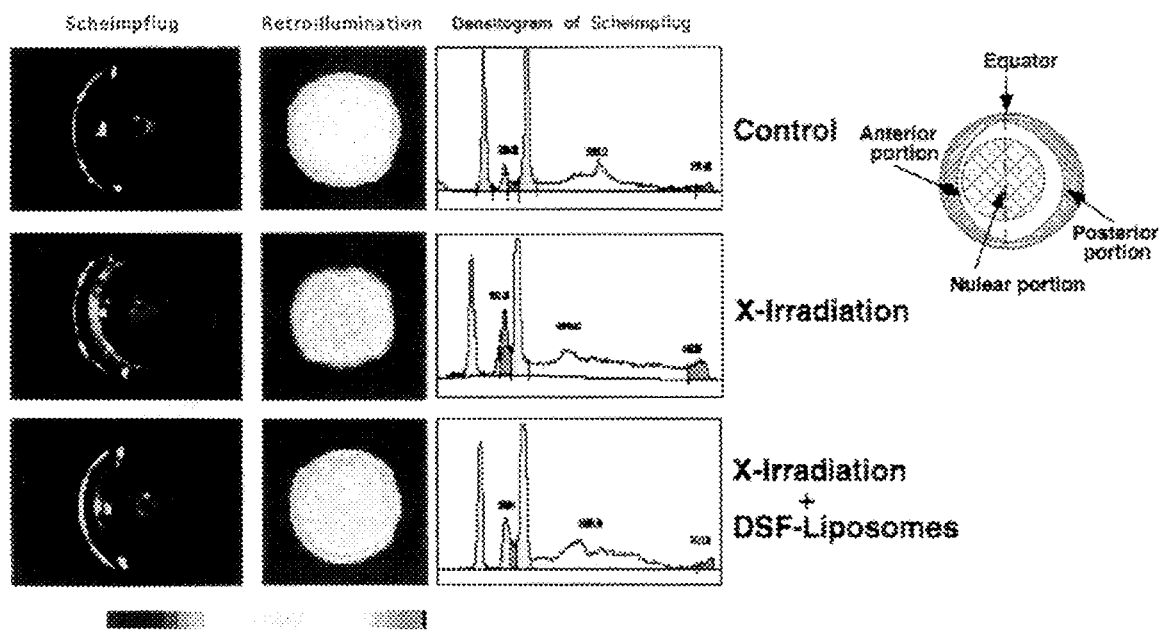
FIG. 9 shows scheimpflug and retroilumination images of X-irradiated rats and effect of DSF against its cataract.

Evaluation of Anti-Cataract Effect of Instillation of DSF-Liposomes on X-Ray Cataracts by Image Analysis FIG. 9 shows the images obtained from rat eyes 6 months after X-irradiation by a Scheimpflug camera. The lenses of X-irradiation control rats were observed strongly opaque in anterior and posterior portions. However, the lenses of DSF-liposome instilled rats were observed to have no or a trace opacity at the two portions mentioned above (FIGS. 9, 10A,B, 11).

Table 6 show the digitized data from the above results analyzed by a Mackintosh program software, NIH Image. The opacities in anterior and posterior portions of lenses with the instillation of DSF-liposomes were lower than those of lenses without drug treatment, though this difference was not significant. Its reason is thought to be that there were high individual differences of responses against X-ray among rats used in this experiment, or the fixings of rat bodies may be not enough to uniformly receive X-irradiation.

TABLE 6

Anterior, Nuclear and Posterior Opacities in Lenses of X-irradiated Pats Treated with or without Anti-Cataract Agents

| | Opacity (count) | | |
| --- | --- | --- | --- |
| | Anterior portion | Nuclear portion | Posterior portion |
| Norm. Control X-Irradiation | 1206 ± 759 | 203397 ± 37889 | 1818 ± 1728 |
| None | 4630 ± 1736 | 259396 ± 25752 | 12720 ± 9449 |
| DSF-liposomes | 3515 ± 1656 | 279951 ± 32227 | 5716 ± 3798 |
| DDC-Na solution | 4707 ± 1494 | 295814 ± 42134 | 9347 ± 5658 |
| GE solution | 3897 ± 2299 | 249074 ± 55147 | 7787 ± 6704 |
| CMZ solution | 4578 ± 2214 | 264612 ± 52206 | 12304 ± 10843 |

Figure 12A:
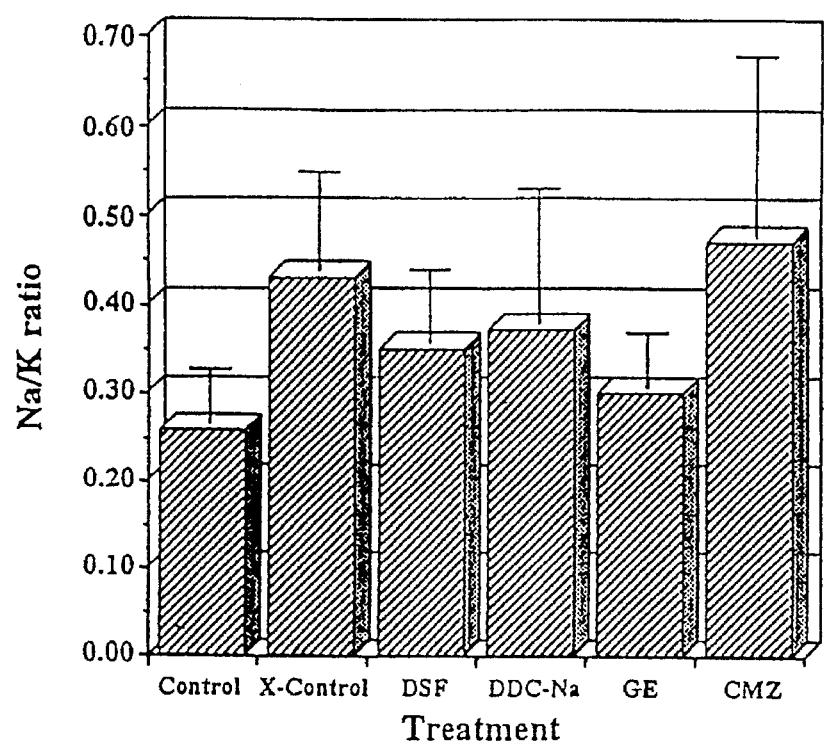
FIGS. 12A and 12B show effects of anti-cataract agents on Na/K ratio (FIGS. A) and Ca (FIG. B) contents in crystalline lenses of X-irradiated rats treated with or without anti-cataract agents.
Figure 12B:
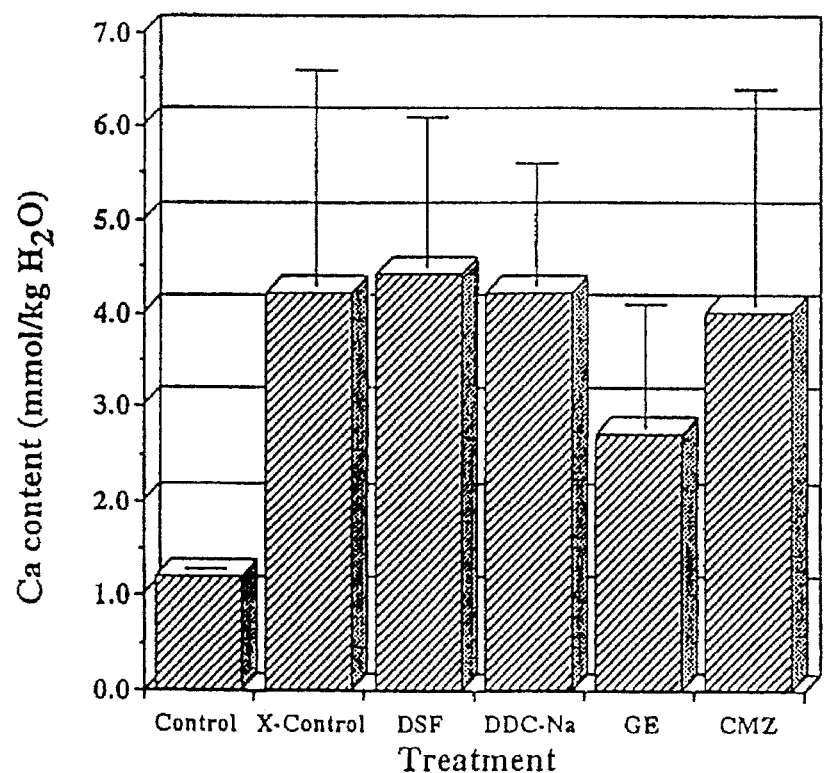

Effects of Instillation of DSF-Liposomes on $Na^+/K^+$ Ratio and $Ca^{2+}$ Content in Crystalline Lenses of X-irradiated Rats Effects of DSF-liposomes on $Na^+/K^+$ ratio and $Ca^{2+}$ contents an X-irradiated rat lenses are shown in Table 7 and FIG. 12. The treatments of DSF-liposomes restored completely the Na⁺/K⁺ ratio and Ca²⁺ contents to the control levels (FIGS. 12A,B)

TABLE 7

Na⁺/K⁺ ratios, Ca²⁺ and GSH Contents in Lenses of X-irradiated
Rats Treated with or without Anti-Cataract Agents

|  | $Na^+/K^+$ ratio | $Ca^{2+}$ content (mmol/kg $H_2O$) | GSH content (μmol/lens) |
|---|---|---|---|
| Control | 0.26 ± 0.06 | 1.2 ± 0 | 135.2 ± 12.0 |
| X-Irradiation |  |  |  |
| None | 0.43 ± 0.11 | 4.2 ± 2.3 | 100.1 ± 12.0 |
| DSF-liposomes | 0.35 ± 0.08 | 4.4 ± 1.6 | 137.3 ± 22.6 |
| DDC-NA solution | 0.37 ± 0.15 | 4.2 ± 1.3 | 126.7 ± 25.3 |
| GE solution | 0.30 ± 0.06 | 2.7 ± 1.3 | 130.6 ± 29.9 |
| CMZ solution | 0.47 ± 0.20 | 4.0 ± 2.3 | 99.7 ± 21.7 |

Figure 13:
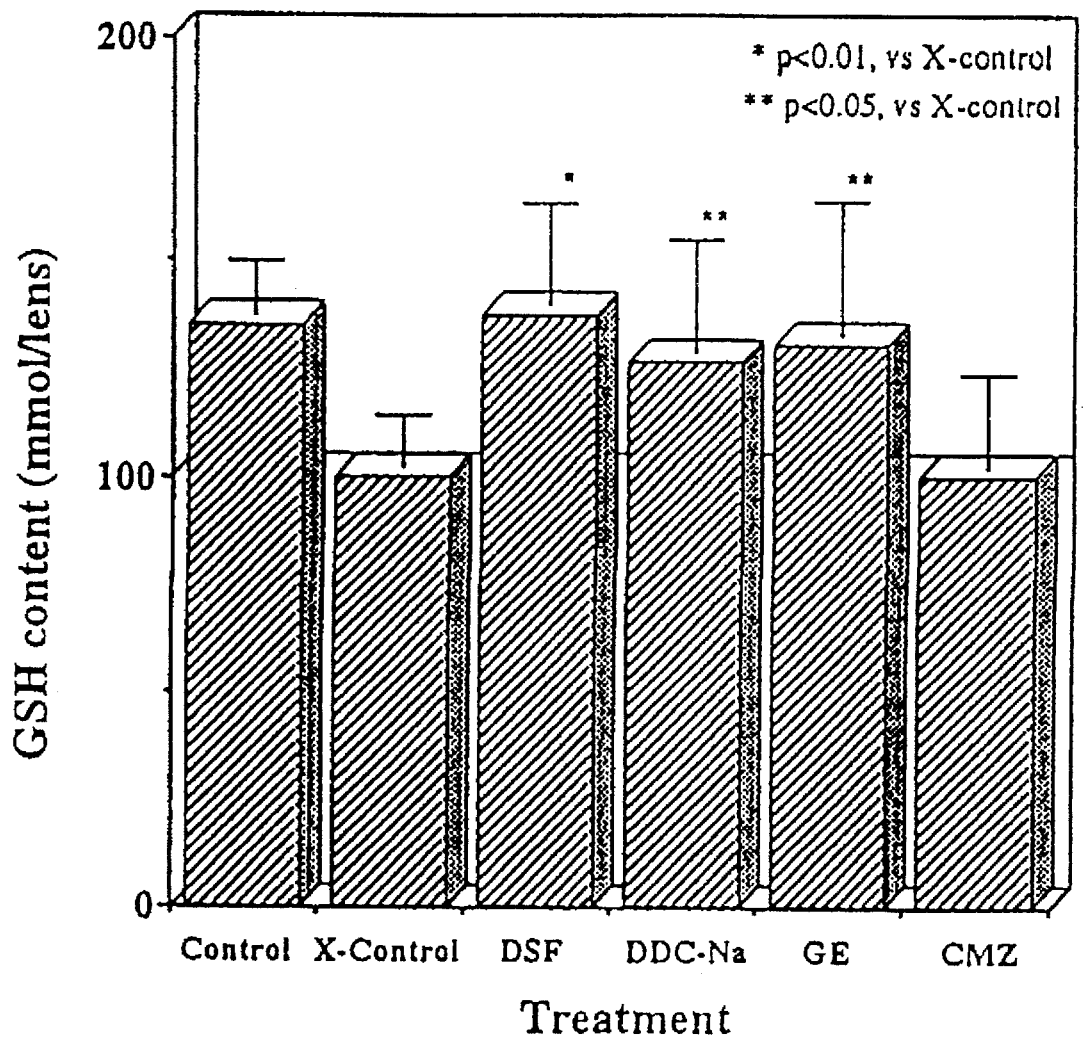
FIG. 13 shows effects of anti-cataract agents on GSH contents in crystalline lenses of X-irradiated rats treated with or without anti-cataract agents.

Effect of Instillation of DSF-Liposomes on GSH
Content in Lenses of X-irradiated Rates GSH contents in the X-irradiated lenses determined by HPLC method are shown in Table 3 and FIG. 13. Restoring of GSH by the instillation of DSF-liposome was observed significantly (FIG. 13).

In Vivo Anti-cataract Experiment of Liposomes
Containing DSF Using Selenite Cataract Rats In this experiment, selenite-induced cataract rats were used as a models of acute cataracts, which relate disorders by radical derivatives generated during various metabolism in mammalian organs.

(1) Materials and Methods

A. Induction of Cataract by Inject of Selenite

Wistar rat pups post natal age 16–18 days were used in this experiment. The injection dose of sodium selenite was 3.28 mg/kg (19 μmol/kg).

B. Image Analysis

Lens opacification was observed by a Scheimpflug camera and recorded at selected time points from 0 to 7 days.

Image Analysis

Opacities of lenses of selenite cataracts were digitized from the data of densitometry integrated areas of the Scheimpflug images. Transparencies of the lenses were digitized from the data of the retroillumination images.

C. Determination of GSH in Rat Lenses

The excised lenses were homogenized with 0.5 ml of purified water by Teflon homogenizer. GSH in the homogenate was determined by the HPLC method followed. Fifty microliter of the lens homogenate were added into 100 μl of acetonitrile containing 100 μg of sodium pantothenate (internal standard) and centrifuged at 12,000 rpm for 10 min. The supernatant solution (10 μl) was injected into a HPLC apparatus, Shimadzu LC-10AD equipped with a column oven, CTO-6A and the chromatography were performed under the conditions; a column of Supersphere 100RP-18 (particle size: 4 μn, column size: 4.0×250 mm), mobile phase of 5% methanol containing 1.0% TFA, flow rate of 1 ml/min, and column temperature at 35° C.

D. Determination of Na⁺, K⁺ and Ca²⁺ in Rat Lenses

Lenses were dried in vacuo at 100° C. for 8 hr, and then digested in 60% nitric acid (100 μl/lens) at 80° C. to degrade organic substances. One milliliter of purified water was added to the digests, and centrifuged at 300 xg for 10 min. Two tenth ml of the supernatant was mixed with 2 ml of purified water, and was used for measurement of Na⁺ and K⁺. One tenth milliliter of 100 μg/ml lanthanum chloride was added to the residual supernatant and used for measurement of Ca²⁺, Na⁺, K⁺ and Ca²⁺ contents in the lenses were determined by atomic absorption spectrometer (Hitachi 180-80, Tokyo, Japan).

(2) Results

Figure 14:
FIG. 14 shows photographs of selnite rats with or without instillation of DSF-liposomes, DSF-suspension and CMZ-liposomes.
Figure 15:
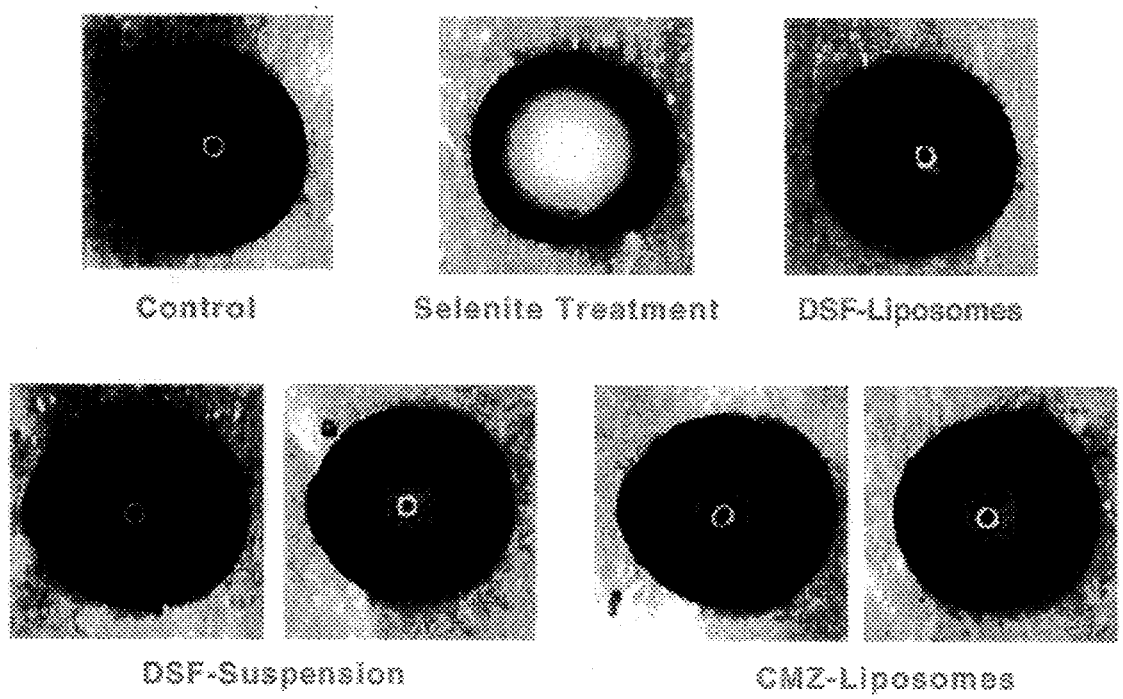
FIG. 15 shows photographs of crystalline lenses of selnite rats with or without instillation of DSF-liposomes, DSF-suspension and CMZ-liposomes.

Photographs for Anti-Cataract Effect of Instillation
of Drugs on Selenite Cataracts FIGS. 14 and 15 show photographs for heads and excised lenses of selenite-induced rats, respectively. High level nuclear cataract were observed in the eyes of selenite treated rat, but no opacity was observed in those instilled eye drops containing DSF-liposomes. Both DSF suspension and CMZ-liposome instilled eyes showed low level nuclear cataract (FIGS. 14 and 16).

Figure 16:
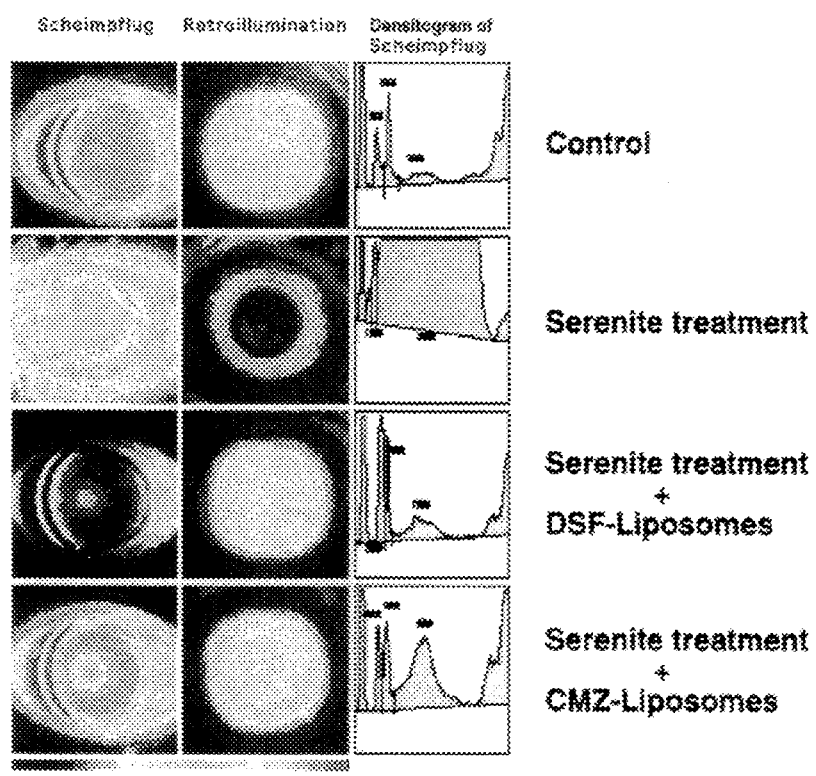
FIG. 16 shows scheimpflug and retroillumination images of selenite cataract rats.

Evaluation of Anti-Cataract Effect of Instillation of
Drugs on Selenite Cataracts by Image Analysis FIG. 16 shows the images obtained from rat eyes a week after injection of selenite by a Scheimpflug camera. The lenses of selenite-treated rats showed strongly opacity in the nuclear portion. On the other hand, the lenses of DSF-liposome instilled rats showed no or a trace opacity at the nuclear portion. The transparency of selenite-treated rat eyes decreased by 60% of those of normal control rats. One the other hand, the transparency of DSF-instilled rat eyes was similar to control rat eyes.

Table 8 show the digitized data from the above results analyzed by a Macintosh software, NIH Image. The opacities in the nuclear portion of lenses with instillation of DSF-liposomes were significantly lower than those of lenses without drug treatment (FIGS. 16 and 17A and 17B)

TABLE 8

Opacities and Transparencies in Lenses of Selenite-induced
Cataract Rats Treated with or without Anti-Cataract Agents

|  | Opacity (count) | Transparency (%) |
|---|---|---|
| Normal Control | 3301 ± 1021 | 95.60 ± 4.01 |
| Selenite Treatment |  |  |
| None | 20683 ± 4659 | 56.24 ± 17.08 |
| DSF-Liposomes | 10170 ± 6305 | 87.41 ± 9.72 |
| DSF-Suspension | 17017 ± 7195 | 69.74 ± 15.26 |
| CMZ-Liposomes | 19617 ± 6163 | 70.12 ± 12.64 |

Figure 18A:
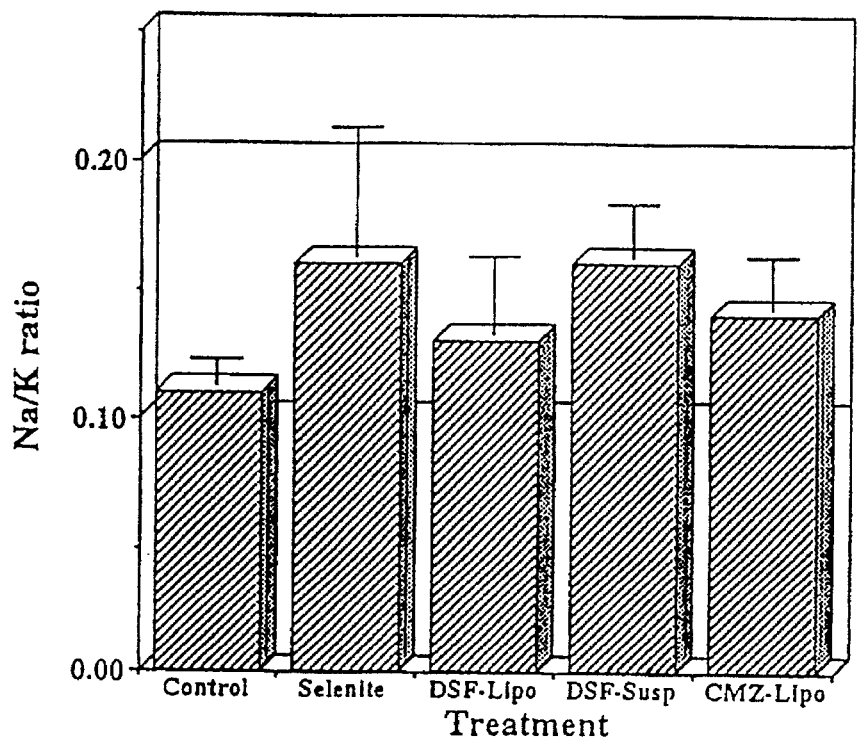
FIGS. 18A and 18B show effects of anti-cataract agents on Na/K ratio (FIG. A) and Ca (FIG. B) contents in crystalline lenses of selenite rats treated with or without anti-cataract agents.
Figure 18B:
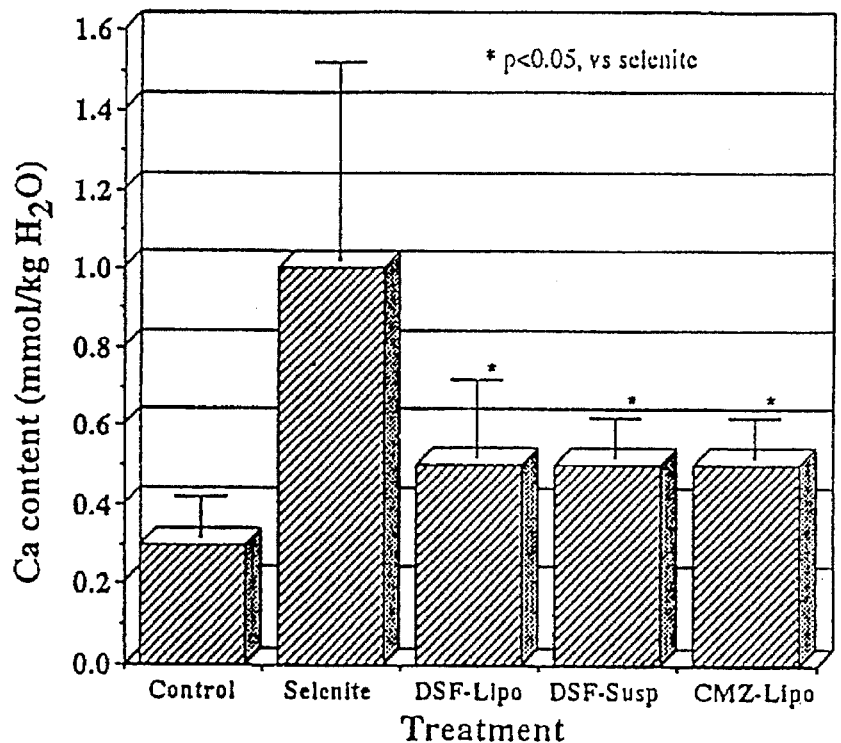

Effects of Instillation of DSF-Liposomes on Na⁺/K⁺
Ratio and Ca²⁺ Content in Lenses of Selenite
Cataract Rats Effects of DSF-liposomes on Na⁺/K⁺ ratio and Ca²⁺ contents in selenite cataract lenses are shown in Table 9 and FIG. 18. The instillation of DSF-liposomes restored completely the Ca²⁺ content to the normal levels. However, no differences were observed between the Na⁺/K⁺ ratios in lenses with and without anti-cataract agents and the ratios were almost same as that in normal rat lens (FIG. 18A and B)

TABLE 9

Na⁺/K⁺ ratios, Ca²⁺ and GSH contents in Lenses of Selenite-
Induced Rats Treated with or without Anti-Cataract Agents

|  | Na⁺/K⁺ ratio | Ca²⁺ content (mmol/kg H₂O) | GSH content (μmol/lens) |
|---|---|---|---|
| Normal Control | 0.11 ± 0.01 | 0.3 ± 0.1 | 125.1 ± 10.1 |
| Selenite Treatment |  |  |  |
| None | 0.16 ± 0.05 | 1.0 ± 0.5 | 99.0 ± 5.4 |
| DSF-Liposomes | 0.13 ± 0.03 | 0.5 ± 0.2 | 111.0 ± 11.3 |
| DSF-Suspension | 0.16 ± 0.02 | 0.5 ± 0.1 | 113.0 ± 14.2 |
| CMZ-Liposomes | 0.14 ± 0.02 | 0.5 ± 0.1 | 110.7 ± 8.3 |

Figure 19:
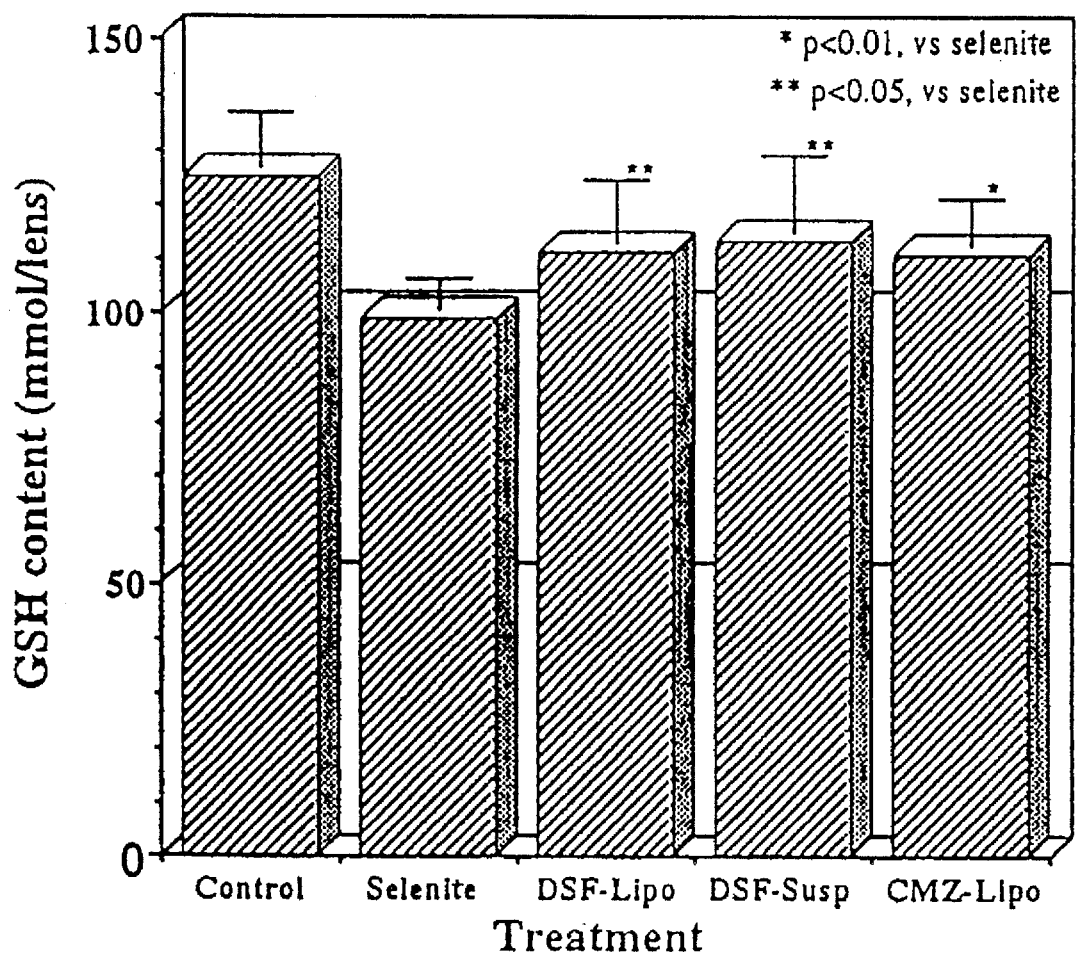
FIG. 19 shows effects of anti-cataract agents on GSH contents in crystalline lenses of selenite rats treated with or without anti-cataract agents.

Effects of Instillation of DSF-Liposomes on GSH
Content in Lenses of Selenite Cataract Rats GSH contents in the selenite cataract lenses determined by the HPLC method were shown in Table 8 and FIG. 19. Restoring of GSH by the instillation of DSF-liposomes, DSF suspension and CMZ-liposomes was observed significantly.

What is claimed is:

1. A pharmaceutical composition for treatment of cataract which comprises fine particles selected from the group consisting of emulsions, nanocapsules, albumin microspheres and liposomes, carrying an anti-cataract agent containing a radical scavenger comprising a disulfide derivative of formula:

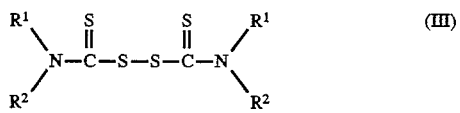

(III)

wherein $R^1$ and $R^2$ are independently a straight or branched lower alkyl which may be substituted by hydroxy, lower alkyloxy or lower alkyl carbonyloxy.

2. The pharmaceutical composition of claim 1 in which said disulfide derivative is disulfiram.

3. The pharmaceutical composition according to claim 1 in which the surface of said fine particles has a lipophilic and positively charged phase.

4. The pharmaceutical composition according to claim 1 in which said fine particles include a lipophilic and positively charged substance in an amount of about 1 to 30% by mole of said fine particles.

5. The pharmaceutical composition according to claim 1 in which said fine particles are liposomes.

6. The pharmaceutical composition according to claim 5 in which said liposomes include natural or semisynthetic phospholipid.

7. The pharmaceutical composition according to claim 1 in which said fine particles are produced by dissolving a fine particle forming material and a lipophilic and positively charged substance in an amount of about 1 to 30% by mole of the total component in an organic medium, and then, in case of said anti-cataract agent being lipophilic, further dissolving said anti-cataract agent in the resultant organic medium, and in case of said anti-cataract agent being water-soluble, dissolving said anti-cataract agent in an aqueous medium and adding the resultant aqueous medium to the resultant organic medium, and in each case forming fine particles to obtain fine particles of which the surface has a lipophilic and positively charged phase.

8. A pharmaceutical composition for treatment of cataract which comprises fine particles selected from the group consisting of emulsions, nanocapsules, albumin microspheres and liposomes, carrying an anti-cataract agent containing a radical scavenger comprising a reducing thiol derivative in which said reducing thiol is a compound of formula:

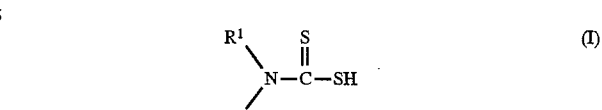

(I)

or

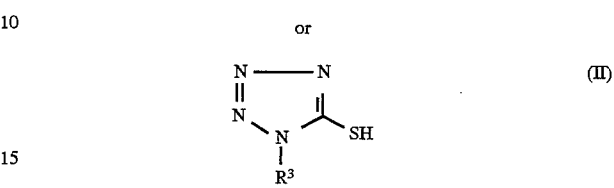

(II)

wherein $R^1$, $R^2$ and $R^3$ are independently a straight or branched lower alkyl which may be substituted by hydroxy, lower alkyloxy or lower alkyl carbonyloxy.

9. The pharmaceutical composition according to claim 8, in which said reducing thiol derivative is selected from the group consisting of diethyl dithiocarbamate, 1-methyl-1H-tetrazol-5-yl-thiol and 1-(2-hydroxyethyl)-1H-tetrazol-5-yl-thiol.

10. The pharmaceutical composition according to claim 8, in which the surface of said fine particles has a lipophilic and positively charged phase.

11. The pharmaceutical composition according to claim 8 in which said fine particles include a lipophilic and positively charged substance in an amount of about 1 to 30% by mole of said fine particles.

12. The pharmaceutical composition according to claim 8 in which said fine particles are liposomes.

13. The pharmaceutical composition according to claim 12, in which said liposomes include natural or semisynthetic phospholipid.

14. The pharmaceutical composition according to claim 8, in which said fine particles are produced by dissolving a fine particle forming material and a lipophilic and positively charged substance in an amount of about 1 to 30% by mole of the total component in an organic medium, and then, in case of an anti-cataract agent being lipophilic, further dissolving said anti-cataract agent in the resultant organic medium, and in case of an anti-cataract agent being water-soluble, dissolving said anti-cataract agent in an aqueous medium and adding the resultant aqueous medium to the resultant organic medium, and in each case forming fine particles to obtain fine particles of which the surface has a lipophilic and positively charged phase.

15. A pharmaceutical composition for treatment of ophthalmic disorders which comprises an agent for treatment of ophthalmic disorders, included in fine particles selected from the group consisting of emulsions, nanocapsules, albumin microspheres and liposomes, the surface of said fine particles having a lipophilic and positively charged phase.

16. The pharmaceutical composition according to claim 15, in which said fine particles include a lipophilic and positively charged substance in an amount of about 1 to 30% by mole of said fine particles.

17. The pharmaceutical composition according to claim 15, in which said fine particles are liposomes.

18. The pharmaceutical composition according to claim 17, in which said liposomes include natural or semisynthetic phospholipid.

19. The pharmaceutical composition according to claim 15 in which said fine particles are produced by dissolving a fine particle forming material and a lipophilic and positively charged substance in an amount of about 1 to 30% by mole of the total component in an organic medium, and then, in case of said agent for treatment of ophthalmic disorders being lipophilic, further dissolving said agent in the resultant organic medium, and in case of said agent for treatment of ophthalmic disorders being water-soluble, dissolving said agent in an aqueous medium, and in each case forming fine particles to obtain fine particles of which the surface has a lipophilic and positively charged phase.

20. A method for treatment of cataract which comprises administering to a subject in need of such treatment, a radical scavenger in an amount effective in treatment of cataract comprising a disulfide derivative of formula:

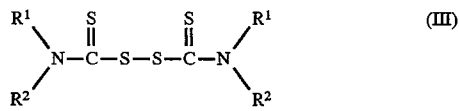

wherein $R^1$ and $R^2$ are independently a straight or branched lower alkyl which may be substituted by hydroxy, lower alkyloxy or lower alkyl carbonyloxy.

21. The method according to claim 20, in which said disulfide derivative is disulfiram.

22. A method for treatment of cataract which comprises administering to a subject in need of such treatment, a radical scavenger in an amount effective in treatment of cataract comprising a reducing thiol derivative in which said reducing thiol is a compound of formula:

or

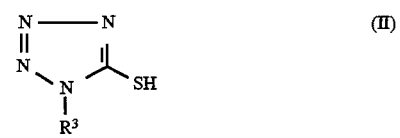

wherein $R^1$ and $R^2$ and $R^3$ are independently a straight or branched lower alkyl which may be substituted by hydroxy, lower alkyloxy or lower alkyl carbonyloxy.

23. The method according to claim 22, in which said reducing thiol derivative is selected from the group consisting of diethyl dithiocarbamate, 1-methyl-1H-tetrazol-5-yl-thiol and 1-(2-hydroxyethyl)-1H-tetrazol-5-yl-thiol.

* * * * *